United States Patent
Kim et al.

(10) Patent No.: US 11,104,878 B2
(45) Date of Patent: *Aug. 31, 2021

(54) LACTIC ACID BACTERIA CAPABLE OF CONTROLLING BLOOD SUGAR AND USE THEREOF

(71) Applicant: University-Industry Cooperation Group of Kyung Hee University, Yongin-si (KR)

(72) Inventors: Dong Hyun Kim, Seoul (KR); Myung Joo Han, Seoul (KR); Su Min Lim, Seoul (KR); Sang Yun Lee, Seoul (KR)

(73) Assignee: UNIVERSITY-INDUSTRY COOPERATION GROUP OF KYUNG HEE UNIVERSITY, Yongin-si (KR)

( * ) Notice: Subject to any disclaimer, the term of this patent is extended or adjusted under 35 U.S.C. 154(b) by 17 days.

This patent is subject to a terminal disclaimer.

(21) Appl. No.: 16/303,320

(22) PCT Filed: Sep. 7, 2016

(86) PCT No.: PCT/KR2016/009995
§ 371 (c)(1),
(2) Date: Nov. 20, 2018

(87) PCT Pub. No.: WO2017/204415
PCT Pub. Date: Nov. 30, 2017

(65) Prior Publication Data
US 2020/0063089 A1    Feb. 27, 2020

(30) Foreign Application Priority Data
May 24, 2016   (WO) ................ PCT/KR2016/005493

(51) Int. Cl.
| | | |
|---|---|---|
| *C12N 1/20* | (2006.01) | |
| *A23L 33/135* | (2016.01) | |
| *A61P 1/16* | (2006.01) | |
| *A61P 3/04* | (2006.01) | |
| *A61P 3/10* | (2006.01) | |
| *A61P 29/00* | (2006.01) | |
| *A61P 1/04* | (2006.01) | |
| *A61K 35/00* | (2006.01) | |
| *C12R 1/225* | (2006.01) | |

(52) U.S. Cl.
CPC ............. *C12N 1/20* (2013.01); *A23L 33/135* (2016.08); *A61P 1/04* (2018.01); *A61P 1/16* (2018.01); *A61P 3/04* (2018.01); *A61P 3/10* (2018.01); *A61P 29/00* (2018.01); *C12N 1/205* (2021.05); *A61K 2035/11* (2013.01); *C12R 2001/225* (2021.05)

(58) Field of Classification Search
CPC ......... C12N 1/20; A23L 33/135; C12R 1/225; A61K 2035/115
See application file for complete search history.

(56) References Cited

FOREIGN PATENT DOCUMENTS

| KR | 100872911 B1 | * 12/2008 |
|---|---|---|
| KR | 10-1010914 B1 | 1/2011 |
| KR | 10-1061219 B1 | 9/2011 |
| KR | 10-2012-0100608 A | 9/2012 |
| KR | 10-1407980 B1 | 6/2014 |
| KR | 10-2015-0098202 A | 8/2015 |
| KR | 10-2016-0108751 A | 9/2016 |

OTHER PUBLICATIONS

Lee et al., "Lactobacillus sakei OK67 ameliorates collagen-induced arthritis in mice by inhibiting NF-κB activation and restoring Th17/Treg cell balance" Journal of functional foods 2015 v. 18 pp. 501-511, abstract (Year: 2015).*
Ji et al., "Modulation of the murine microbiome with a concomitant anti-obesity effect by Lactobacillus rhamnosus GG and Lactobacillus sakei NR28", Beneficial Microbes, Mar. 2012; 3(1): 13-22 (Year: 2012).*
U.S. Appl. No. 16/303,401 (Year: 2018).*
Int'l Search Report dated Feb. 20, 2017 in Int'l Application No. PCT/KR2016/005493.
Lim et al, "Lactobacillus sakei OK67 ameliorates high-fat diet-induced blood glucose intolerance and obesity in mice by inhibiting gut microbiota lipopolysaccharide production and inducing colon tight junction protein expression," Nutrition Research, vol. 36, pp. 337-348 (Apr. 2016).
NCBI Reference Sequence No. KC416998.1 (Sep. 2013).
Kook et al, "Effect of Gamma-aminobutyric Acid Produced by Lactobacillus sakei B2-16 on Diet and Exercise in High Fat Diet-induced Obese Rats," Food Science and Biotechnology, vol. 23, No. 6, pp. 1965-1970 (2014).
Cah et al, "Final Report of Studies on the antiinflammatory efficacy and anti-obesity/diabetic effect of functional materials producing microbial strains isolated from fermented food (Kimchi)," (Jul. 17, 2013).
Database GenBank, Apr. 1, 2009, Lactobacillus curvatus gene for 16S ribosomal RNA, partial sequence, strain: KH9, AB494734.1.
Int'l Search Report dated Feb. 20, 2017 in Int'l Application No. PCT/KR2016/009995.
Lee, Sang-Yun, "The anti-inflammatory effects of Lactobacillus sakei OK67 in mice with collagen II-induced arthritis," Department of Life and Nanopharmaceutical Sciences Kyung Hee University (Feb. 2016).

(Continued)

*Primary Examiner* — Ruth A Davis
(74) *Attorney, Agent, or Firm* — Sughrue Mion, PLLC

(57) ABSTRACT

A *Lactobacillus* species strain isolated from kimchi or human feces is described. The particular *Bacillus* species strain described is highly safe by being isolated from kimchi or human feces and has various functionalities, such as excellent blood sugar control activity, anti-obesity activity, blood cholesterol-lowering activity, blood neutral lipid-lowering activity, arteriosclerosis-inhibiting activity or inflammation-inhibiting activity. Accordingly, the particular *Bacillus* species strain described can be used as a useful food and drug material for preventing, alleviating or treating a metabolic syndrome including diabetes, obesity, fatty liver, glycosuria, hyperlipidemia, cardiovascular disease, hypertension, arteriosclerosis and/or diabetes, an inflammatory disease, and the like.

3 Claims, 34 Drawing Sheets
Specification includes a Sequence Listing.

(56) References Cited

OTHER PUBLICATIONS

Lee et al, "Lactobacillus sakei OK67 ameliorates collagen-induced arthritis in mice by inhibiting NF-Kappa-B activation and restoring Th17/Treg cell balance," Journal of Functional Foods, vol. 18, pp. 501-511 (2015).
Moon et al., Anticariogenic activities of Lactobacillus sakei K-7 isolated from kimchi, 26 Korean society for biotechnology and bioengineering journal 513-516 (2011).
Lee et al., Functional properties of Lactobacillus strains isolated from kimchi, 145 International Journal of Food Microbiology 155-161 (2011).
Siu, Mass of a Bacterium—The Physics Factbook, 1 Page https://hypertextbook.com/facts/2003/LouisSiu.shtml (Apr. 23, 2019).
Kim et al., Heterofermentative Lactic Acid Bacteria Dominate in Korean Commercial Kimchi, 25(2) Food. Sci. Biotechnol. 541-545 (2016).

* cited by examiner

LACTIC ACID BACTERIA CAPABLE OF CONTROLLING BLOOD SUGAR AND USE THEREOF

CROSS-REFERENCE TO RELATED APPLICATION

This application is a Section 371 of International Application No. PCT/KR2016/009995, filed Sep. 7, 2016, which was published in the Korean language on Nov. 30, 2017, under International Publication No. WO 2017/204415 A1, which claims priority under 35 U.S.C. § 119(b) to International Application No. PCT/KR2016/005493, filed May 24, 2016, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing 689288.0012", creation date of Nov. 20, 2018, and having a size of 2.3 MB. The sequence listing submitted via EFS-Web is part of the specification and is herein incorporated by reference in its entirety.

TECHNICAL FIELD

The present invention relates to a novel lactic acid bacterium, and more particularly to, a novel lactic acid bacterium which is isolated from kimchi or human feces and has various functionalities, such as blood sugar control effect, antiobesity effect, blood cholesterol-lowering effect, blood neutral lipid-lowering effect, arteriosclerosis inhibiting effect, immunoregulatory effect, immunopotentiating effect, and inflammation inhibiting effect. The present invention also relates to various uses of novel lactic acid bacteria, and more particularly, to a use of novel lactic acid bacteria for the prevention, alleviation or treatment of diabetes, obesity, a metabolic syndrome, inflammatory diseases and the like.

BACKGROUND ART

As humanity develops into a prosperous society gradually, the lifestyle is rapidly westernized, and the pattern of disease is also changing dramatically. Especially, abdominal obesity, hyperlipidemia, diabetes and hypertension are increasing in modern people. Such diseases are called lifestyle-related diseases in terms of diseases caused by lifestyle changes. Obesity, hyperlipidemia, diabetes, and hypertension among lifestyle-related diseases are known to be important risk factors for cardiovascular diseases, and metabolic syndrome refers to the simultaneous occurrence of these cardiovascular risk factors. In other words, metabolic syndrome refers to a state of high insulin resistance, a high risk of diabetes and cardiovascular disease, and in the presence of metabolic syndrome, the risk of developing cardiovascular disease is more than twice as high, and the risk of developing diabetes increases by more than 10 times. In addition, the prevalence rate of various chronic diseases such as arthritis and cancer is increasing due to increase in lifestyle-related diseases.

The increase in lifestyle-related diseases is largely due to the westernized diet and lack of exercise. Especially, the change of diet leads to changes in the human digestive tract microbiota, which causes the endotoxin produced by the digestive tract microbiota in the digestive tract to increase. Increased endotoxin in the digestive tract causes digestive tract inflammation, increased absorption of endotoxin into the body, and promotes migration of macrophages to adipose tissue and the like, leading to obesity or hyperglycemia. Thus, in case of controlling endotoxins produced by the digestive tract microbiota, blood sugar may be controlled and ultimately improve or treat diabetes.

Diabetes is a typical chronic disease, and is a chronic disease that causes microvascular complications such as retinas, kidneys and nerves, and macrovascular complications such as stroke, angina, myocardial infarction and peripheral vascular disease due to various metabolic disorders including glucose. Diabetes may be treated by drug therapy, exercise therapy, and diet therapy. Depending on the patient's symptoms, insulin medicines and various blood sugar control agents are used. However, diabetes is a complex disease illustrating characteristics such as excessive glucose production in the liver, insulin resistance, and reduced glucose disposal ability in muscle and adipocytes. Therefore, specific treatments alone cannot prevent the occurrence of various side effects. Among them, drug therapy uses insulin and chemicals, there is a constant problem for the side effects of drug use and patient tolerance. Recently, there is a need for studies to prevent, improve, or treat diabetes by using natural products which are dietary and have few side effects in the treatment of diabetes.

In accordance with this trend, researches on the prevention or treatment of abdominal obesity, hyperlipidemia, diabetes, hypertension and the like have been conducted recently using lactic acid bacteria. For example, Korean Patent Registration Publication No. 10-1061219 discloses a pharmaceutical composition for prevention and treatment of diabetes including an artichoke fermented extract fermented with *Lactobacillus* sp. as an active ingredient. In addition, Korean Patent Registration Publication No. 10-1010914 discloses *Lactobacillus plantarum* NUC LG42 strain (accession number: KCCM 10940P) for use in any one selected from the group consisting of body weight and fat reduction, plasma and liver lipid and carnitine improvement, blood leptin, insulin concentration reduction, and memory improvement. In addition, Korean Patent Registration Publication No. 10-1407980 discloses a health functional food for alleviating hyperinsulinemia, hyperglycemia and hypertriglyceridemia containing *Lactobacillus curvatus* HY7601 (accession number: KCTC 11456BP) and *Lactobacillus plantarum* KY1032 (accession number: KCCM10430) as active ingredients characterized by having an effect of reducing the levels of blood insulin, resistin, glucose, C-peptide and triglyceride.

DISCLOSURE

Technical Problem

The present invention has been derived from this conventional background. It is an object of the present invention to provide a novel lactic acid bacterium which may inhibit the proliferation of intestinal microorganisms that secrete endotoxins or inhibit endotoxin production of intestinal microorganisms to regulate blood sugar.

Another object of the present invention is to provide various uses of novel lactic acid bacteria.

Technical Solution

In order to develop an anti-diabetic material having higher safety than synthetic chemicals, the present inventors screened numerous lactic acid bacteria from kimchi or human feces and found that certain *Lactobacillus* species strains could inhibit the proliferation of intestinal microorganisms that secrete endotoxins or inhibit endotoxin production of intestinal microorganisms to regulate blood sugar, and completed the present invention.

In order to achieve one object of the present invention, one embodiment of the present invention is a *Lactobacillus sakei* including a nucleotide sequence as set forth in SEQ ID NO.: 1 as a 16S rDNA, and provides a lactic acid bacterium having blood sugar control activity. The *Lactobacillus sakei* is preferably a *Bacillus* which is positive in Gram strain, and uses ribose, galactose, glucose, fructose, mannose, mannitol, sorbitol, α-methyl-D mannoside, N-acetyl-glucosamine, amygdalin, arbutin, esculin, salicin, cellobiose, maltose, lactose, melibiose, sucrose, trehalose, melezitose, gentiobiose and turanose as a carbon source. In addition, the *Lactobacillus sakei* preferably has one or more activities selected from the group consisting of an anti-obesity activity, a blood cholesterol-lowering activity, a blood neutral lipid-lowering activity, arteriosclerosis-inhibiting activity, a tight junction protein expression inducing activity, an immunoregulatory activity, an immunopotentiating activity, or an inflammation-inhibiting activity in addition to blood sugar control activity. In addition, the *Lactobacillus sakei* is preferably *Lactobacillus sakei* OK67 (accession number: KCCM 11670P). In addition, the *Lactobacillus sakei* preferably inhibits the proliferation of intestinal microorganisms that secrete endotoxins or inhibits endotoxin production of intestinal microorganisms, thereby lowering blood sugar.

In order to achieve another object of the present invention, one embodiment of the present invention provides a composition for lowering blood sugar including *Lactobacillus sakei* including the nucleotide sequence as set forth in SEQ ID NO.: 1 as a 16S rDNA, a culture thereof, a lysate thereof or an extract thereof as an active ingredient. In addition, one embodiment of the present invention provides an anti-obesity composition including *Lactobacillus sakei* including the nucleotide sequence as set forth in SEQ ID NO: 1 as a 16S rDNA, a culture thereof, a lysate thereof, or an extract thereof as an active ingredient. In addition, one embodiment of the present invention provides a pharmaceutical composition for use in the prevention or treatment of diabetes, obesity, hypertriglyceridemia, hypercholesterolemia, hyperlipidemia, dyslipidemia, arteriosclerosis or metabolic syndrome in which at least two of the above diseases occur simultaneously, including *Lactobacillus sakei* including the nucleotide sequence as set forth in SEQ ID NO: 1 as a 16S rDNA, a culture thereof, a lysate thereof, or an extract thereof as an active ingredient. In addition, one embodiment of the present invention provides a food composition for use in the prevention or treatment of diabetes, obesity, hypertriglyceridemia, hypercholesterolemia, hyperlipidemia, dyslipidemia, arteriosclerosis or metabolic syndrome in which at least two of the above diseases occur simultaneously, including *Lactobacillus sakei* including the nucleotide sequence as set forth in SEQ ID NO: 1 as a 16S rDNA, a culture thereof, a lysate thereof, or an extract thereof as an active ingredient.

In order to achieve another object of the present invention, one embodiment of the present invention provides a composition for immune regulation or immune enhancement including *Lactobacillus sakei* including the nucleotide sequence as set forth in SEQ ID NO.: 1 as a 16S rDNA, a culture thereof, a lysate thereof or an extract thereof as an active ingredient.

In addition, one embodiment of the present invention provides a pharmaceutical composition for preventing or treating inflammatory diseases including *Lactobacillus sakei* including the nucleotide sequence as set forth in SEQ ID NO.: 1 as a 16S rDNA, a culture thereof, a lysate thereof or an extract thereof as an active ingredient. In addition, one embodiment of the present invention provides a food composition for preventing or alleviating inflammatory diseases including *Lactobacillus sakei* including the nucleotide sequence as set forth in SEQ ID NO.: 1 as a 16S rDNA, a culture thereof, a lysate thereof or an extract thereof as an active ingredient. At this time, the inflammatory disease is preferably selected from gastritis, gastric ulcer, arthritis, and colitis.

In addition, one embodiment of the present invention provides a pharmaceutical composition for preventing or treating liver damage including *Lactobacillus sakei* including the nucleotide sequence as set forth in SEQ ID NO.: 1 as a 16S rDNA, a culture thereof, a lysate thereof or an extract thereof as an active ingredient. In addition, one embodiment of the present invention provides a food composition for preventing or treating liver damage including *Lactobacillus sakei* including the nucleotide sequence as set forth in SEQ ID NO.: 1 as a 16S rDNA, a culture thereof, a lysate thereof or an extract thereof as an active ingredient. At this time, the liver damage is preferably selected from the group consisting of hepatitis, fatty liver, and liver cirrhosis.

Advantageous Effects

The particular *Lactobacillus* species strain according to the present invention is isolated from kimchi or human feces and has high safety, and has various functionalities, such as excellent blood sugar control activity, anti-obesity activity, blood cholesterol-lowering activity, blood neutral lipid-lowering activity, arteriosclerosis-inhibiting activity, tight junction protein expression-inducing activity, immunoregulatory activity, immunopotentiating activity, and inflammation-inhibiting activity. Therefore, the particular *Lactobacillus* species strain according to the present invention may be used as a food and drug material for preventing, alleviating or treating a metabolic syndrome including diabetes, obesity, fatty liver, glycosuria, hyperlipidemia, cardiovascular disease, hypertension, arteriosclerosis, diabetes or obesity, an inflammatory disease, and the like, or for immune regulation, immune enhancement or inhibition of inflammatory response.

DESCRIPTION OF DRAWINGS

In FIGS. 3 to 17, "LFD" refers to a group fed with a low-fat diet, "LFD-67" refers to a group fed with a low-fat diet and administered *Lactobacillus sakei* OK67 with a dose of 1×10$^9$ CFU/mouse, "HFD" refers to a group fed with a high-fat diet, and "HFD-OK67" refers to a group fed with a high-fat diet and administered *Lactobacillus sakei* OK67 with a dose of 1×10$^9$ CFU/mouse.

In FIGS. 18 and 19, "NOR" refers to a group to which arthritis was not induced by collagen but to which a vehicle was administered, "AC" refers to a group to which arthritis was induced by collagen and a vehicle was administered, and "AO" refers to a group in which arthritis was induced by collagen and *Lactobacillus sakei* OK67 strain was administered together with a vehicle.

In FIGS. 20 to 22, "CIA" refers to collagen-induced arthritis, and "OK 67" refers to *Lactobacillus sakei* OK67 strain.

In FIGS. 23 to 26, "CIA" refers to collagen-induced arthritis, "OK 67" refers to *Lactobacillus sakei* OK67 strain, and "IP" refers to ibuprofen.

DETAILED DESCRIPTION OF EMBODIMENT

Figure 1:
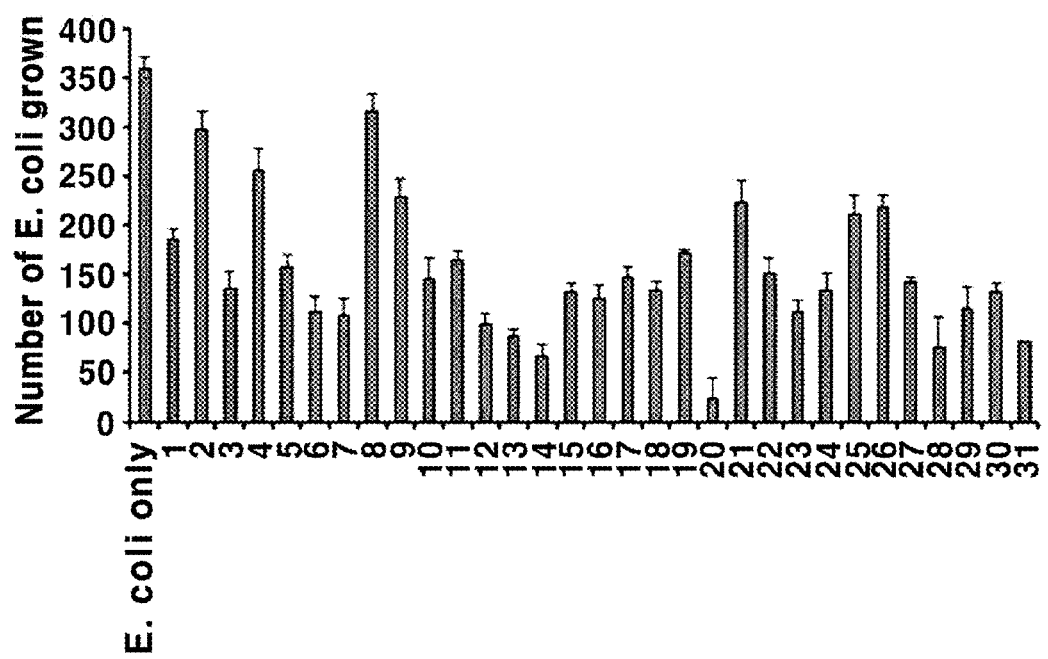
FIG. 1 is a graph illustrating the effect of lactic acid bacteria isolated from cabbage kimchi, radish kimchi, green onion kimchi and human feces on the proliferation of *E. coli*.

Hereinafter, terms used in the present invention will be described.

As used herein, "culture" means a product obtained by culturing a microorganism in a known liquid medium or solid medium, and includes a microorganism.

The terms "pharmaceutically acceptable" and "sitologically acceptable" in the present invention is meant not significantly irritating the organism and not interfering with the biological activity and properties of the administered active substance.

As used herein, the term "prevention" refers to any action that inhibits the symptoms of a particular disease or delays progression upon administration of the composition of the present invention.

As used herein, the term "treatment" refers to any action that improves or beneficially changes the symptoms of a particular disease upon administration of the composition of the present invention.

As used herein, the term "improvement" refers to any action that at least reduces the parameter associated with the condition being treated, for example, the degree of symptoms.

As used herein, the term "administration" is meant to provide any desired composition of the present invention to a subject by any suitable method. Herein, the term "subject" means any animal such as a human, a monkey, a dog, a goat, a pig, or a mouse having a disease in which symptoms of a specific disease can be improved by administering the composition of the present invention.

As used herein, the term "pharmaceutically effective amount" means an amount sufficient to treat a disease at a reasonable benefit or risk rate applicable to medical treatment, which is determined by the type of disease of a subject, severity, activity of drugs, sensitivity to drugs, the time of administration, the route of administration and the rate of excretion, the duration of treatment, and factors including drugs used simultaneously and other factors well known in the medical fields.

Hereinafter, the present invention will be described in detail.

One aspect of the present invention relates to a novel lactic acid bacterium having a blood sugar control activity (for example, hypoglycemic activity).

The novel lactic acid bacterium according to one embodiment of the present invention is *Lactobacillus sakei* including the nucleotide sequence as set forth in SEQ ID NO: 1 as a 16S rDNA and having a blood sugar control activity. The *Lactobacillus sakei* is preferably a *Bacillus* which is positive in Gram strain, and uses ribose, galactose, glucose, fructose, mannose, mannitol, sorbitol, α-methyl-D mannoside, N-acetyl-glucosamine, amygdalin, arbutin, esculin, salicin, cellobiose, maltose, lactose, melibiose, sucrose, trehalose, melezitose, gentiobiose and turanose as a carbon source. In addition, the *Lactobacillus sakei* preferably has one or more activities selected from the group consisting of an anti-obesity activity, a blood cholesterol-lowering activity, a blood neutral lipid-lowering activity, arteriosclerosis-inhibiting activity, or an inflammation-inhibiting activity in addition to blood sugar control activity. In addition, the *Lactobacillus sakei* is preferably *Lactobacillus sakei* OK67 (accession number: KCCM 11670P). In addition, the *Lactobacillus sakei* preferably inhibits the proliferation of intestinal microorganisms that secrete endotoxins or inhibits endotoxin production of intestinal microorganisms, thereby lowering blood sugar. In addition, the *Lactobacillus* species strain of the present invention may be isolated from kimchi. For example, *Lactobacillus sakei* OK67 was isolated from radish kimchi. In addition, the *Lactobacillus* species strain of the present invention preferably has the nucleotide sequence as set forth in SEQ ID NO: 2 as a whole genome sequence.

Another aspect of the invention relates to various uses of the novel lactic acid bacteria. For example, the present invention provides a composition for lowering blood sugar including *Lactobacillus sakei* including the nucleotide sequence as set forth in SEQ ID NO.: 1 as a 16S rDNA, a culture thereof, a lysate thereof or an extract thereof as an active ingredient, as described as a use of the novel lactic acid bacteria. In addition, the present invention provides an anti-obesity composition including *Lactobacillus sakei* including the nucleotide sequence as set forth in SEQ ID NO: 1 as a 16S rDNA, a culture thereof, a lysate thereof, or an extract thereof as an active ingredient, as described as a use of the novel lactic acid bacteria. In addition, the present invention provides a pharmaceutical composition for use in the prevention or treatment of diabetes, obesity, hypertriglyceridemia, hypercholesterolemia, hyperlipidemia, dyslipidemia, arteriosclerosis or metabolic syndrome in which at least two of the above diseases occur simultaneously, including *Lactobacillus sakei* including the nucleotide sequence as set forth in SEQ ID NO: 1 as a 16S rDNA, a culture thereof, a lysate thereof, or an extract thereof as an active ingredient, as described as a use of the novel lactic acid bacteria. In addition, the present invention provides a food composition for use in the prevention or alleviation of diabetes, obesity, hypertriglyceridemia, hypercholesterolemia, hyperlipidemia, dyslipidemia, arteriosclerosis or metabolic syndrome in which at least two of the above diseases occur simultaneously, including *Lactobacillus sakei* including the nucleotide sequence as set forth in SEQ ID NO: 1 as a 16S rDNA, a culture thereof, a lysate thereof, or an extract thereof as an active ingredient, as described as a use of the novel lactic acid bacteria. At this time, the metabolic syndrome refers to a disease in which various metabolic diseases such as diabetes and obesity occur simultaneously in one person, and narrowly refers to a lipid-related metabolic syndrome. In the present invention, the metabolic syndrome is preferably a disease in which one or more diseases selected from the group consisting of diabetes and obesity and one or more diseases selected from the group consisting of hypertriglyceridemia, hypercholesterolemia, hyperlipidemia, dyslipidemia, cardiovascular disease, hypertension, and arteriosclerosis occur simultaneously. In addition, the present invention provides a composition for immune regulation or immune enhancement including *Lactobacillus sakei* including the nucleotide sequence as set forth in SEQ ID NO.: 1 as a 16S rDNA, a culture thereof, a lysate thereof or an extract thereof as an active ingredient, as described as a use of the novel lactic acid bacteria. The *Lactobacillus sakei* OK67 strain according to the present invention may regulate the immunity by restoring the balance of Th17/Treg cells, and thus may improve allergic diseases such as autoimmune diseases such as rheumatoid arthritis, and atopic dermatitis, and may boost the weakened level of immunity. In addition, the present invention provides a pharmaceutical composition for preventing, alleviating or treating inflammatory diseases including *Lactobacillus sakei* including the nucleotide sequence as set forth in SEQ ID NO.: 1 as a 16S rDNA, a culture thereof, a lysate thereof or an extract thereof as an active ingredient, as described as a use of the novel lactic acid bacteria. At this time, the inflammatory disease is not greatly limited to its type as long as it is a disease caused by the inflammatory reaction, and is preferably selected from the group consisting of gastritis, gastric ulcer, arthritis, and colitis. In addition, the present invention provides a composition for preventing, alleviating or treating liver damage including *Lactobacillus sakei* including the nucleotide sequence as set forth in SEQ ID NO.: 1 as a 16S rDNA, a culture thereof, a lysate thereof or an extract thereof as an active ingredient, as described as a use of the novel lactic acid bacteria. In this case, the liver damage refers to a state in which the liver function is not normal due to an external factor or an internal factor and is preferably selected from the group consisting of hepatitis, fatty liver, and cirrhosis. In addition, the hepatitis includes both non-alcoholic hepatitis and alcoholic hepatitis. In addition, the fatty liver includes both non-alcoholic fatty acid and alcoholic fatty acid. In the present invention, a culture of lactic acid bacteria is a product obtained by culturing a *Lactobacillus* species strain in a medium. The culture medium may be selected from known liquid culture media or solid culture media, for example, an MRS liquid medium, an MRS agar medium, a BL agar medium. In the present invention, the composition may be specified to a pharmaceutical composition, a food additive, a food composition (in particular, a functional food composition), or a feed additive depending on the purpose of uses and aspects, and the contents of specific *Lactobacillus* species, which is an active ingredient in a composition, may be adjusted in various ranges depending on the specific form of the composition, the purpose of uses and aspects.

The content of the novel lactic acid bacterium, the culture thereof, the lysate thereof or the extract thereof as an active ingredient in the pharmaceutical composition according to the present invention is not particularly limited and may be, for example, 0.01 to 99% by weight, preferably 0.5 to 50% by weight, more preferably 1 to 30% by weight based on the total weight of the composition. In addition, the pharmaceutical composition according to the present invention may further include, in addition to the active ingredient, an additive such as a pharmaceutically acceptable carrier, excipient or diluent. Examples of carriers, excipients and diluents that may be included in the pharmaceutical composition of the present invention include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oil. The pharmaceutical composition of the present invention may further include one or more kinds of known active ingredients effective in preventing or treating diabetes, obesity, fatty liver, hyperlipidemia, cardiovascular disease, hypertension, arteriosclerosis, metabolic syndrome, inflammatory disease or immunodeficiency disease, in addition to a novel lactic acid bacterium, a culture thereof, a lysate thereof or an extract thereof. The pharmaceutical composition of the present invention may be formulated into a formulation for oral administration or parenteral administration by a conventional method, and in case of a preparation, it may be prepared using diluents or excipients such as fillers, extenders, binders, wetting agents, disintegrants, and surfactants which are usually used. Solid preparations for oral administration include tablets, pills, powders, granules, capsules and the like, which may be prepared by mixing at least one excipient such as starch, calcium carbonate, sucrose, lactose, gelatin with an active ingredient. In addition to simple excipients, lubricants such as magnesium stearate and talc may also be used. Liquid preparations for oral administration include suspensions, oral solutions, emulsions and syrups. Various excipients such as wetting agents, sweetening agents, flavor agents, and preservatives may be included in addition to water and liquid paraffin, which are simple diluents commonly used. Preparations for parenteral administration may include sterile aqueous solutions, non-aqueous solutions, suspensions, emulsions, lyophilized preparations, and suppositories. As for the non-aqueous solvent and the suspending solvent, propylene glycol, polyethylene glycol, vegetable oil such as olive oil, injectable ester such as ethyl oleate may be used. As the base of suppositories, witepsol, macrogol, tween 61, cacao paper, laurinum, glycerogelatin and the like may be used. Further, it may be preferably prepared according to each disease or ingredient using a suitable method in the pertinent field or a method described in Remington's Pharmaceutical Science (recent edition), Mack Publishing Company, Easton Pa. The pharmaceutical composition of the present invention may be administered orally or parenterally to a mammal including a human according to a desired method. Examples of the parenteral administration include external dermal application, intraperitoneal injection, rectal injection, subcutaneous injection, intravenous injection, intramuscular injection or intra-thoracic injection. The dosage of the pharmaceutical composition of the present invention is not greatly limited as long as it is a pharmaceutically effective amount, and the range may vary depending on the patient's body weight, age, sex, health condition, diet, administration time, administration method, excretion rate, and severity of a disease. The typical daily dose of the pharmaceutical composition of the present invention is not greatly limited, but is preferably 0.1 to 3000 mg/kg, more preferably 1 to 2000 mg/kg, based on the active ingredient, and may be administered once a day or several times a day.

In addition, the content of the novel lactic acid bacteria, the culture thereof, the lysate thereof or the extract thereof as an active ingredient in the food composition according to the present invention is 0.01 to 50% by weight, preferably 0.1 to 25% by weight, and more preferably 0.5 to 10% by weight based on the total weight of the composition, but is not limited thereto. The food composition of the present invention may be in the form of a pill, a powder, a granule, an infusion, a tablet, a capsule, or a liquid. Specific examples of the food include meat, sausage, bread, chocolate, candy, snack, confectionery, pizza, ramen, other noodles, gums, dairy products including ice cream, various soups, beverages, tea, functional water, drinks, alcoholic beverages and vitamin complexes, and include all the healthy foods in a common sense. The food composition of the present invention may include, in addition to the active ingredient, a sitologically acceptable carrier, various flavors or natural carbohydrates as an additional ingredient. In addition, the food composition of the present invention may include various nutrients, vitamins, electrolytes, flavors, colorants, pectic acids and its salts, alginic acid and its salts, organic acids, protective colloid thickeners, pH adjusters, stabilizers, preservatives, glycerin, alcohols, a carbonating agent used in a carbonated drink, and the like. In addition, the food composition of the present invention may include fruit flesh for the production of natural fruit juices, fruit juice drinks and vegetable drinks. These ingredients may be used independently or in combination. The above-mentioned natural carbohydrates are sugar alcohols such as monosaccharides such as glucose and fructose, disaccharides such as maltose and sucrose, polysaccharides such as dextrin and cyclodextrin, and xylitol, sorbitol and erythritol. Natural flavors such as thaumatin and *stevia* extract, synthetic flavors such as saccharin and aspartame may be used as the flavor agent.

Hereinafter, the present invention will be described in more detail with reference to examples. However, the following examples are intended to clearly illustrate the technical features of the present invention and do not limit the scope of protection of the present invention.

1. Isolation and Identification of Lactic Acid Bacteria (1) Isolation of Lactic Acid Bacteria from Kimchi Cabbage kimchi, radish kimchi, and green onion kimchi were each crushed and the crushed liquid was suspended in an MRS liquid medium (MRS Broth; Difco, USA). Then, the supernatant was taken to be inoculated into MRS agar medium (Difco, USA) and was anaerobically incubated at 37° C. for about 48 hours. Then, colony-forming strains were isolated.

(2) Isolation of Lactic Acid Bacteria from Human Feces

Human feces were put in a GAM liquid medium (GAM broth; Nissui Pharmaceutical, Japan) and were suspended. Then, the supernatant was taken to be inoculated into a BL agar medium (Nissui Pharmaceutical, Japan), and was anaerobically incubated at 37° C. for about 48 hours. Then, colony-forming strains were isolated.

(3) Identification of Selected Lactic Acid Bacteria

The physiological characteristics and 16S rDNA sequence of strains isolated from kimchi or human feces were analyzed and the species of the strains were identified and were given strain names. Table 1 below shows the management numbers and the names of the strains of the lactic acid bacteria isolated from cabbage kimchi, radish kimchi, green onion kimchi and human feces. In Table 1 below, the lactic acid bacteria of Management Nos. 1, 3, 5, 7, 9, 11, 13, 17, 20, 22 and 25 were isolated from cabbage kimchi, the lactic acid bacteria of Management Nos. 2, 4, 6, 8, 10, 14, 19 and 21 were isolated from radish kimchi, the lactic acid bacteria of Management Nos. 12, 15 and 18 were isolated from green onion kimchi, and lactic acid bacteria of Management Nos. 24, 26, 27, 28, 29 and 30 were isolated from human feces.

TABLE 1

| Management Nos. | Names of strains |
|---|---|
| 1 | *Leuconostoc mesenteroides* OK1 |
| 2 | *Leuconostoc mesenteroides* OK15 |
| 3 | *Lactobacillus curvatus* OK21 |
| 4 | *Lactobacillus curvatus* OK25 |
| 5 | *Lactobacillus brevis* OK11 |
| 6 | *Lactobacillus brevis* OK12 |
| 7 | *Lactobacillus acidophilus* OK1 |
| 8 | *Lactobacillus acidophilus* OK7 |
| 9 | *Lactobacillus lactis* OK1 |
| 10 | *Lactobacillus lactis* OK2 |
| 11 | *Lactobacillus helveticus* OK1 |
| 12 | *Lactobacillus helveticus* OK2 |
| 13 | *Lactobacillus plantarum* OK23 |
| 14 | *Lactobacillus plantarum* OK32 |
| 15 | *Lactobacillus plantarum* OK36 |
| 16 | *Lactobacillus plantarum* OK37 |
| 17 | *Lactobacillus sakei* OK26 |
| 18 | *Lactobacillus sakei* OK45 |
| 19 | *Lactobacillus sakei* OK67 |
| 20 | *Lactobacillus fermentum* OK19 |
| 21 | *Lactobacillus fermentum* OK21 |
| 22 | *Lactobacillus gasseri* OK1 |
| 23 | *Lactobacillus gasseri* OK2 |
| 24 | *Lactobacillus johnsonii* OK1 |
| 25 | *Lactobacillus johnsonii* OK2 |
| 26 | *Lactobacillus paracasei* OK2 |
| 27 | *Lactobacillus paracasei* OK9 |
| 28 | *Lactobacillus reuteri* OK1 |
| 29 | *Lactobacillus ruminis* OK1 |
| 30 | *Lactobacillus ruminis* OK17 |

Among the strains listed in Table 1 above, *Lactobacillus sakei* OK67 is an anaerobic bacterium that is positive in Gram strain, and the carbon source availability among physiological characteristics is as shown in Table 2 below. In Table 2 below, the carbon source availability of *Lactobacillus sakei* OK67 was analyzed by sugar fermentation test using API Kit (model name: API 50 CHL; manufacturer: BioMerieux's, USA). In addition, in the following table, "+" represents the case where the carbon source availability is positive, "−" represents the case where the carbon source availability is negative, "±" represents the case where the carbon source availability is ambiguous, and the blank represents the non-measurement.

TABLE 2

| | Name of strains | | |
|---|---|---|---|
| Carbon source | *Lactobacillus sakei* OK67 | DSM20017 (ATCC15521)[a] | *Lactobacillus sakei* K-7[b] |
|---|---|---|---|
| glycerol | − | | |
| erythritol | ± | | |
| D-arabinose | ± | | |
| L-arabinose | − | + | − |
| D-ribose | + | + | |
| D-xylose | − | | |
| L-xylose | − | − | |
| adonitol | − | | |
| methyl-BD-xylopyranosicle | − | | |
| D-galactose | + | + | − |
| D-glucose | + | + | |
| D-fructose | + | + | |
| D-mannose | + | + | |
| L-sorbose | − | | |
| rhamnose | − | − | |
| dulcitol | − | | |
| inositol | − | | |
| mannitol | + | | |
| sorbitol | + | | |
| α-methyl-D-mannoside | + | | |
| α-methyl-D-glucoside | − | − | |
| N-acetyl-glucosamine | + | + | |
| amygdalin | + | | |
| arbutin | + | − | |
| esculin | + | + | |
| salicin | + | + | |
| cellobiose | + | − | |
| maltose | + | + | ± |
| lactose | + | − | |
| melibiose | + | + | |
| sucrose | + | + | + |
| trehalose | + | + | |
| inulin | − | | |
| melezitose | + | | |
| raffinose | − | | |
| starch | − | | |
| glycogen | − | | |
| xylitol | − | ± | |
| gentiobiose | + | | |
| D-turanose | + | | |
| D-lyxose | − | | |
| D-tagatose | − | | |
| D-fucose | − | | |
| L-fucose | − | | |
| D-arabitol | − | | |
| L-arabitol | − | | |
| gluconate | ± | ± | |
| 2-keto-gluconate | − | | |
| 5-keto-gluconate | − | | |

[a] McLeod et al., Diversity of *Lactobacillus* strains investigated by phenotypic and genotypic methods. Systematic and applied microbiology 2008; 31: 393-403.
[b] Moon et al., Anticariogenic activities of *Lactobacillus sakei* K-7 isolated from kimchi. Korean society for biotechnology and bioengineering journal 2011; 26: 513-516.

In addition, 16S rDNA was measured as a chemotaxonomical characteristic of *Lactobacillus sakei* OK67, and as a result, it was found to have the nucleotide sequence as set forth in SEQ ID NO: 1. The 16S rDNA nucleotide sequence of *Lactobacillus sakei* OK67 was identified by BLAST search of Genebank (http://www.ncbi.nlm.nih.gov/). As a result, *Lactobacillus sakei* (*Lactobacillus sakei*) strain having the same 16S rDNA nucleotide sequence was not detected and showed 99% homology with 16S rDNA partial sequence of *Lactobacillus sakei* NBRC 15893 (NCBI ACCESSION: NR 113821).

2. Selection of Lactic Acid Bacteria Inhibiting the Proliferation of *E. coli* Producing Endotoxin (1) Experimental Method Any one selected from *E. coli* cultured in a TSB (tryptic soy broth) medium in advance and lactic acid bacteria isolated from cabbage kimchi, radish kimchi, green opinion kimchi and human feces was inoculated into a TSB (tryptic soy broth) medium all together in an amount of $1 \times 10^5$ CFU and $1 \times 10^5$ CFU, respectively, and cultured at 37° C. for about 24 hours. Thereafter, a mixed strain culture medium of *E. coli* and lactic acid bacteria was diluted $10^6$ times, and 0.1 ml of the diluted culture medium was inoculated into a DHL medium and cultured at 37° C. for about 24 hours. Thereafter, the number of *E. coli* in the final culture solution was measured. As a control group, *E. coli* alone was inoculated into a TSB (tryptic soy broth) medium in an amount of $1 \times 10^5$ CFU and cultured instead of mixed bacteria of *E. coli* and lactic acid bacteria, and then the number of *E. coli* in the final culture solution was measured by going through the same process.

(2) Measurement Result

FIG. 1 is a graph illustrating the effect of lactic acid bacteria isolated from cabbage kimchi, radish kimchi, green onion kimchi, and human feces on the proliferation of *E. coli*. As illustrated in FIG. 1, *Lactobacillus sakei* OK67 exhibited the best ability to inhibit the proliferation of *E. coli*, followed by *Lactobacillus plantarum* OK23, *Lactobacillus parasakei* OK9, and *Lactobacillus ruminis* OK17.

3. Selection of Lactic Acid Bacteria that Inhibit Endotoxin Production in the Digestive Tract Microflora (1) Experimental Method The intestinal flora that were cultured in a GAM liquid medium (GAM broth; Nissui Pharmaceutical, Japan) in advance, and any one selected from the lactic acid bacteria which showed excellent ability to inhibit the proliferation of *E. Coli* [*Lactobacillus sakei* OK67, *Lactobacillus plantarum* OK23, *Lactobacillus paracasei* OK9 and *Lactobacillus ruminis* OK17] were inoculated into a GAM liquid medium (GAM broth; Nissui Pharmaceutical Japan), which is an anaerobic medium, in an amount of $1 \times 10^8$ CFU and $1 \times 10^5$ CFU, respectively, and cultured anaerobically at 37° C. for about 24 hours. Thereafter, the culture solution was treated with ultrasonic waves for about 1 hour to destroy the extracellular membrane of the bacteria, and centrifuged under the condition of 5000×g to obtain a supernatant. Thereafter, the content of LPS (lipopolysaccharide), which is a typical endotoxin present in the supernatant, was measured by LAL (Limulus Amoebocyte Lysate) assay kit (manufacturer: Cape Cod Inc., USA). As a control group, the intestinal flora was inoculated into a GAM liquid medium (GAM broth; Nissui Pharmaceutical, Japan), an anaerobic medium in an amount of $1 \times 10^8$ CFU and cultured instead of mixed bacteria of internal flora and lactic acid bacteria, and then the content of LPS (lipopolysaccharide) present in the supernatant was measured by going through the same process.

(2) Measurement Result

Figure 2:
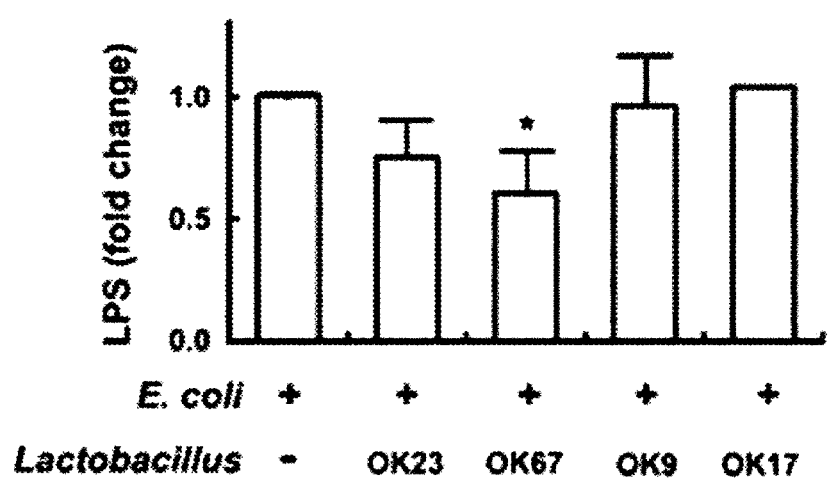
FIG. 2 is a graph illustrating the effect of lactic acid bacteria having excellent ability to inhibit the proliferation of *E. coli* [*Lactobacillus sakei* OK67, *Lactobacillus plantarum* OK23, *Lactobacillus parasakei* OK9, *Lactobacillus ruminis* OK17] on the production of endotoxin in intestinal flora.

FIG. 2 is a graph illustrating the effect of lactic acid bacteria having excellent ability to inhibit the proliferation of *E. coli* [*Lactobacillus sakei* OK67, *Lactobacillus plantarum* OK23, *Lactobacillus parasakei* OK9, *Lactobacillus ruminis* OK17] on the production of endotoxin in intestinal flora. In FIG. 2, the content of LPS (lipopolysaccharide) is shown as a relative multiple of the control group. As illustrated in FIG. 2, just like the result of the ability to inhibit the proliferation of *E. coli*, the ability of intestinal flora to inhibit endotoxin production was the most superior in *Lactobacillus sakei* OK67, followed by *Lactobacillus plantarum* OK23, *Lactobacillus parasakei* OK9, and *Lactobacillus ruminis* OK17.

4. In-Vivo Experiments on the Hypoglycemic Effect of Lactic Acid Bacteria (1) Experimental Method A total of 28 mice of 5-week-old male C57BL/6J were divided into two groups. Low-fat diet (product model name: D12450B; supplier: Research Diets, Inc., New Brunswick, N.J.) in which 10% of the total calorie is fat was administered for 4 weeks in a low-fat diet group (n=14), and high-fat diet (product model: D12492; supplier: Research Diets, Inc., New Brunswick, N.J.) in which 60% of the total calorie is fat was administered for 4 weeks in a high-fat diet group (n=14). Thereafter, the low-fat diet group was divided into two groups (LFD, LFD-67) by 7 mice each. The LFD group was administered low-fat diet and saline solution was administered orally daily for 4.5 weeks (31 days). *Lactobacillus sakei* OK67 strain was orally administered at a daily dose of $1 \times 10^9$ CFU for 4.5 weeks (31 days) at the time of administering low-fat diet to the LFD-67 group, and the experiment was terminated the next day. In addition, the high-fat diet group was divided into two groups (HFD, HFD-67) by 7 mice each. The HLFD group was administered high-fat diet and saline solution was administered orally daily for 4.5 weeks (31 days). *Lactobacillus sakei* OK67 strain was orally administered at a daily dose of $1 \times 10^9$ CFU for 4.5 weeks (31 days) at the time of administering high-fat diet to the HFD-67 group, and the experiment was terminated the next day. The number of oral administration of *Lactobacillus sakei* OK67 strain was 6 days on a basis of one week. During the experimental period, the mice were raised in a breeding environment at a temperature of 20±2° C., a humidity of 50±5% and a light-dark cycle of 12 hours. The content of blood sugar, plasma insulin, plasma endotoxin and fecal endotoxin was measured at the end of the experiment and the oral glucose tolerance test was performed 5 days before the end of the experiment.

Figure 3:
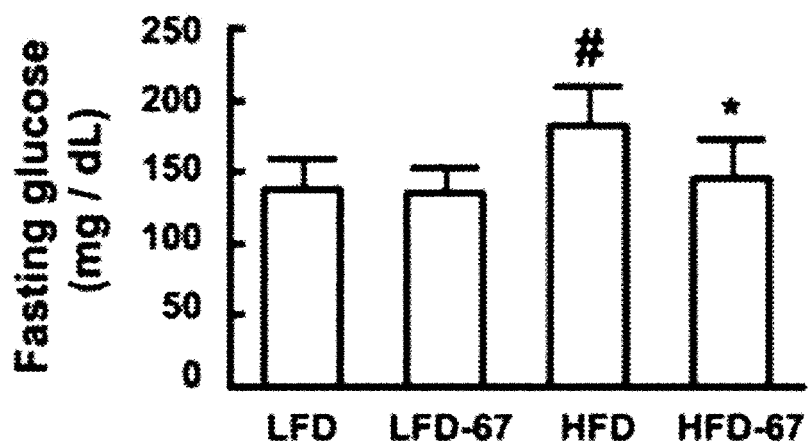
FIG. 3 is a graph illustrating the effect of *Lactobacillus sakei* OK67 on the blood sugar level of a model animal in which obesity was induced by a high-fat diet by experimental groups.

(2) Measurement of Blood Sugar, Plasma Insulin, Plasma Endotoxin and Fecal Endotoxin Content About 0.5 µl of blood was collected from the tail end of the mice and the blood sugar was measured using a kit for measuring glucose (manufacturer: ASAN PHARM. CO. LTD., Korea). FIG. 3 is a graph illustrating the effect of *Lactobacillus sakei* OK67 on the blood sugar level of a model animal in which obesity was induced by a high-fat diet by experimental groups. As illustrated in FIG. 3, the level of blood sugar of a group administered *Lactobacillus sakei* OK67 strain with a high-fat diet were significantly lower than that fed with high-fat diets alone.

Figure 4:
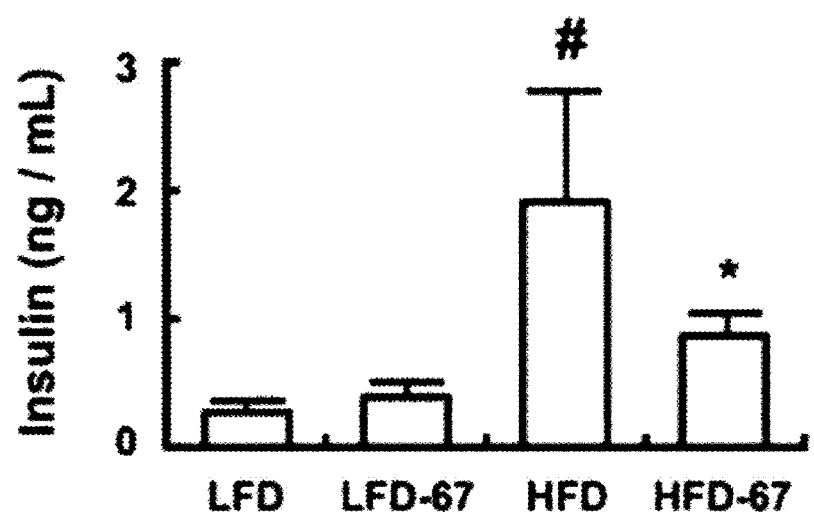
FIG. 4 is a graph illustrating the effect of *Lactobacillus sakei* OK67 on the plasma insulin level of a model animal in which obesity was induced by a high-fat diet by experimental groups.

Plasma insulin was measured using a mouse insulin ELISA kit (LINCO Research, St. Charles, Mo.). FIG. 4 is a graph illustrating the effect of *Lactobacillus sakei* OK67 on the plasma insulin level of a model animal in which obesity was induced by a high-fat diet by experimental groups. As illustrated in FIG. 4, the plasma insulin content of a group fed with *Lactobacillus sakei* OK67 strain with a high-fat diet was significantly lower than that fed with high-fat diets alone.

Figure 5:
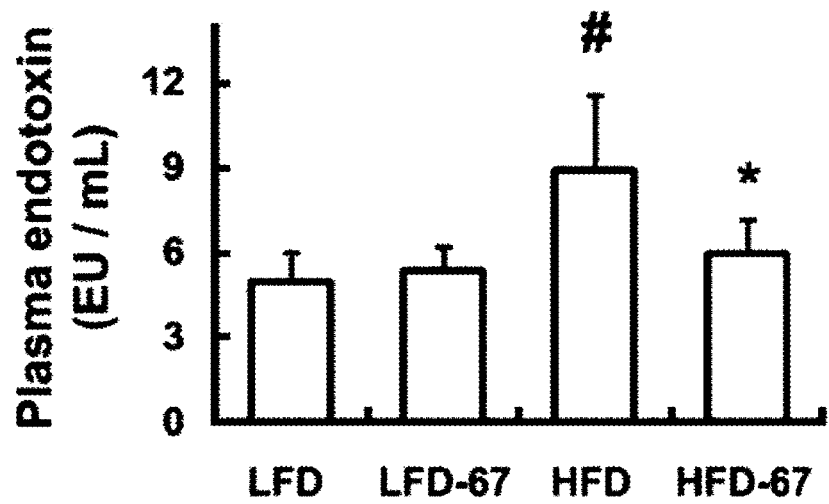
FIG. 5 is a graph illustrating the effect of *Lactobacillus sakei* OK67 on plasma endotoxin content of a model animal in which obesity was induced by a high-fat diet by experimental groups.
Figure 6:
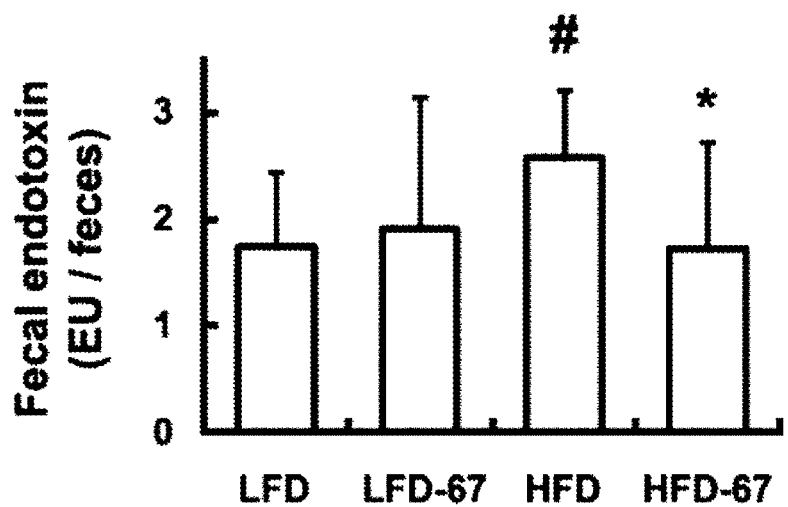
FIG. 6 is a graph illustrating the effect of *Lactobacillus sakei* OK67 on fecal endotoxin content of a model animal in which obesity was induced by a high-fat diet by experimental groups.

FIG. 5 is a graph illustrating the effect of *Lactobacillus sakei* OK67 on plasma endotoxin content of a model animal in which obesity was induced by a high-fat diet by experimental groups, and FIG. 6 is a graph illustrating the effect of Lactobacillus sakei OK67 on fecal endotoxin content of a model animal in which obesity was induced by a high-fat diet by experimental groups. As illustrated in FIGS. 5 and 6, plasma endotoxin content and fecal endotoxin content of a group fed with Lactobacillus sakei OK67 strain with a high-fat diet was significantly lower than that fed with high-fat diets alone.

(3) Oral Glucose Tolerance Test (OGTT)

Five days before the end of the experiment, the experimental animals were fasted for 6 hours, and glucose was orally administered at a volume of 2 g/kg body weight. Then, blood was collected from the tail at 0, 15, 30, 60, 90 and 120 minutes, and glucose concentration was measured. During the oral glucose tolerance test, the experimental animals were given a stable environment and water was allowed to ingest freely. In addition, the area under the glucose-time curve (AUC) was calculated using the following formula.

$$AUC=0.5 \times (0.5 \times C0 + C15 + C30 + C60 + C90 + 0.5 \times C120)$$

In the above formula, C0, C15, C30, C60, C90 and C120 are glucose concentrations measured at 0 minute, 15 minutes, 30 minutes, 60 minutes, 90 minutes and 120 minutes in an orderly manner, respectively.

Figure 7:
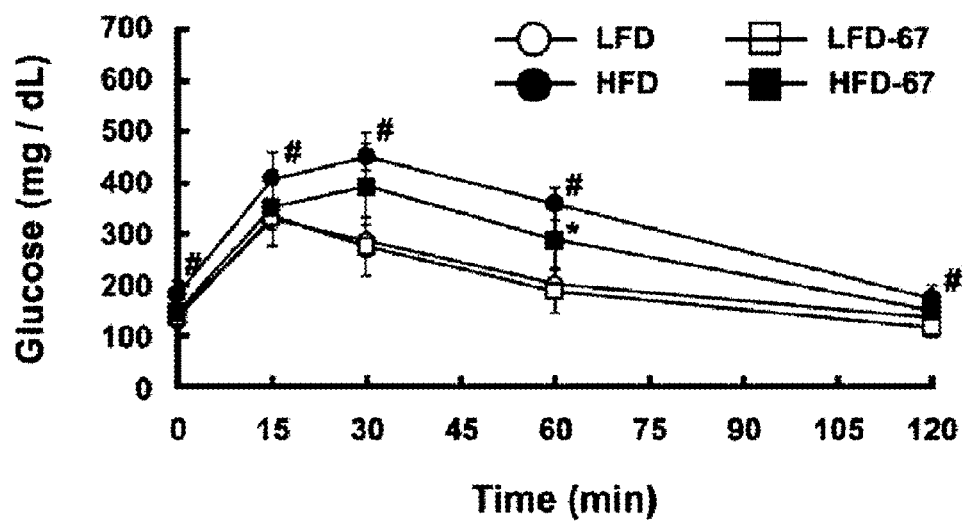
FIG. 7 is a graph illustrating the effect of *Lactobacillus sakei* OK67 on oral glucose tolerance test of a model animal in which obesity was induced by a high-fat diet by experimental groups.
Figure 8:
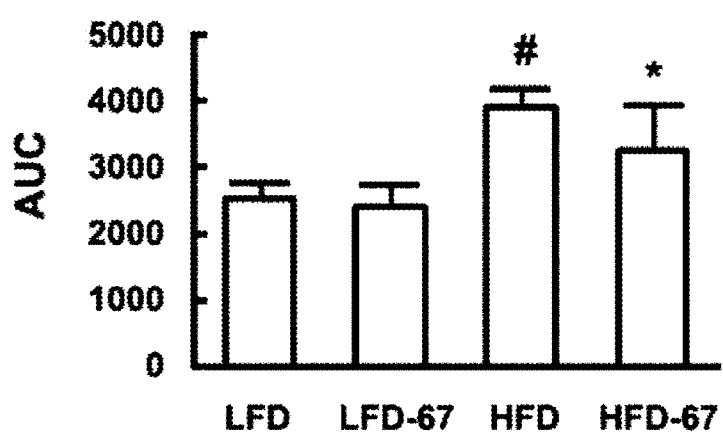
FIG. 8 is a graph illustrating the glucose tolerance test result of FIG. 7 as AUC (area under the glucose-time curve).

FIG. 7 is a graph illustrating the effect of Lactobacillus sakei OK67 on oral glucose tolerance test of a model animal in which obesity was induced by a high-fat diet by experimental groups, and FIG. 8 is a graph illustrating the glucose tolerance test result of FIG. 7 as AUC (area under the glucose-time curve). As illustrated in FIGS. 7 and 8, the AUC of a group fed with Lactobacillus sakei OK67 strain with a high-fat diet was significantly lower than that fed with high-fat diets alone.

5. In-Vivo Experiments on the Anti-Obesity Effect of Lactic Acid Bacteria (1) Experimental Method A total of 28 mice of 5-week-old male C57BL/6J were divided into two groups. Low-fat diet (product model name: D12450B; supplier: Research Diets, Inc., New Brunswick, N.J.) in which 10% of the total calorie is fat was administered for 28 days in a low-fat diet group (n=14), and high-fat diet (product model: D12492; supplier: Research Diets, Inc., New Brunswick, N.J.) in which 60% of the total calorie is fat was administered for 28 days in a high-fat diet group (n=14). Thereafter, the low-fat diet group was divided into two groups (LFD, LFD-67) by 7 mice each. The LFD group was administered low-fat diet and saline solution was administered orally daily for 31 days. Lactobacillus sakei OK67 strain was orally administered at a daily dose of $1 \times 10^9$ CFU for 31 days at the time of administering low-fat diet to the LFD-67 group, and the experiment was terminated the next day. In addition, the high-fat diet group was divided into two groups (HFD, HFD-67) by 7 mice each. The HLFD group was administered high-fat diet and saline solution was administered orally daily for 31 days. Lactobacillus sakei OK67 strain was orally administered at a daily dose of $1 \times 10^9$ CFU for 31 days at the time of administering high-fat diet to the HFD-67 group, and the experiment was terminated the next day. The number of oral administration of Lactobacillus sakei OK67 strain was 6 days on a basis of 7 days. During the experimental period, the mice were raised in a breeding environment at a temperature of 20±2° C., a humidity of 50±5% and a light-dark cycle of 12 hours. After the experiment, the experimental animals were sacrificed by cardiac puncture, and colon and epididymal fat (EF) were extracted and additionally analyzed.

(2) Body Weight Change and Weight Change of Adipose Tissue

Figure 9:
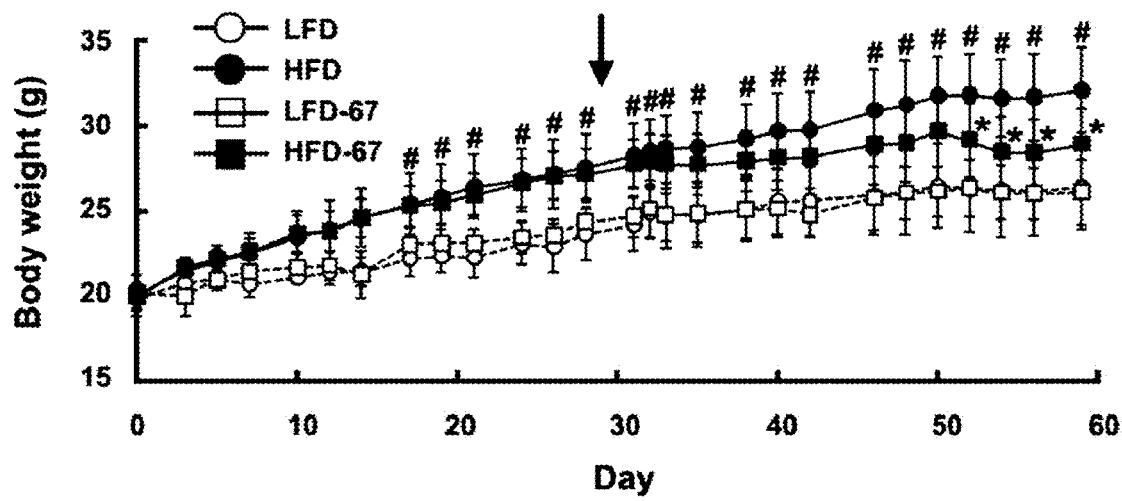
FIG. 9 is a graph illustrating the effect of *Lactobacillus sakei* OK67 on changes in body weight of a model animal in which obesity was induced by a high-fat diet by experimental groups.
Figure 10:
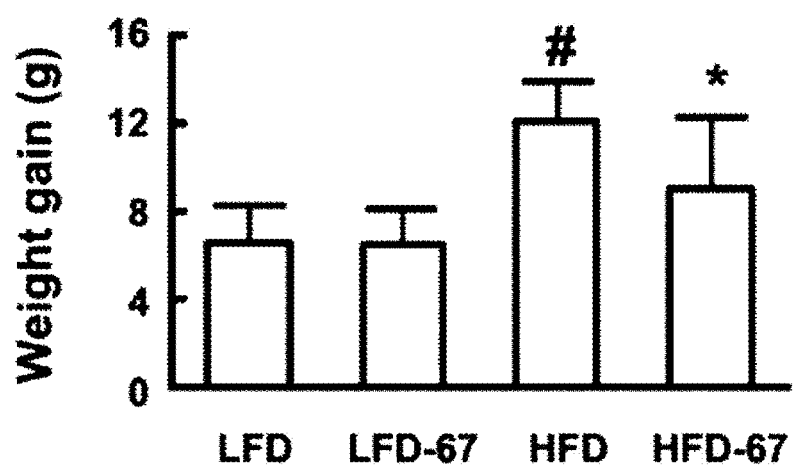
FIG. 10 is a graph illustrating the effect of *Lactobacillus sakei* OK67 on body weight gain of a model animal in which obesity was induced by a high-fat diet by experimental groups.
Figure 11:
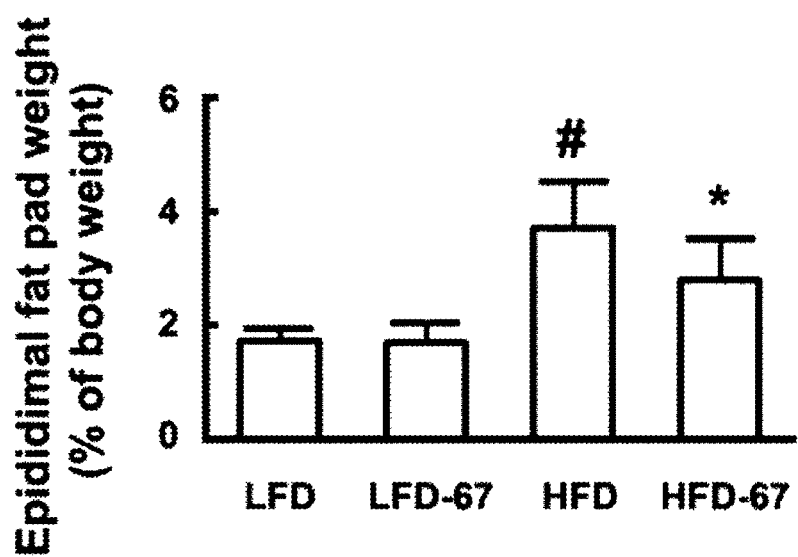
FIG. 11 is a graph illustrating the effect of *Lactobacillus sakei* OK67 on the weight change of epididymal adipose tissue of a model animal in which obesity was induced by a high-fat diet by experimental groups.

FIG. 9 is a graph illustrating the effect of Lactobacillus sakei OK67 on changes in body weight of a model animal in which obesity was induced by a high-fat diet by experimental groups, and FIG. 10 is a graph illustrating the effect of Lactobacillus sakei OK67 on weight gain a model animal in which obesity was induced by a high-fat diet by experimental groups. The arrow in the downward direction in FIG. 9 represents the time when Lactobacillus sakei OK67 was orally administered. In addition, FIG. 11 is a graph illustrating the effect of Lactobacillus sakei OK67 on the weight change of epididymal adipose tissue of a model animal in which obesity was induced by a high-fat diet by experimental groups. As illustrated in FIGS. 9 to 11, in the group to which Lactobacillus sakei OK67 strain was orally administered together with the high-fat diet after induction of obesity, the body weight was significantly reduced compared with the group fed only with high-fat diets after induction of obesity, and the weight of adipose tissue was shown to be far lower.

(3) Measurement of Plasma Triglyceride, Plasma Total Cholesterol and Plasma HDL Cholesterol Content Plasma triglyceride, plasma cholesterol and plasma HDL content of the experimental animals that induced obesity and received lactic acid bacteria for 35 days were measured as follows.

Plasma triglyceride was measured using a kit for measuring triglyceride (ASAN PHARM. CO. LTD., Korea). 1.5 ml of the enzyme solution and 10 μl of plasma were added to the test tube, followed by stirring. Thereafter, the sample was heated in a water bath at 37° C. for 10 minutes with a standard solution having a triglyceride content of 0, 75, 150, 225 and 300 mg/dl, respectively, and the absorbance at 550 nm was measured and quantified by colorimetry. In addition, plasma total cholesterol was measured using a kit for total cholesterol measurement (ASAN PHARM. CO. LTD., Korea). 1.5 ml of the enzyme solution and 10 μl of plasma were added to the test tube, followed by stirring. Thereafter, the sample was heated in a water bath at 37° C. for 10 minutes with a standard solution having a total cholesterol content of 0, 75, 150, 225 and 300 mg/dl, respectively, and the absorbance at 550 nm was measured and quantified by colorimetry. In addition, plasma HDL cholesterol was measured using a kit for HDL cholesterol measurement (ASAN PHARM. CO. LTD., Korea). After adding 50 μl of needle-shaped reagent to 50 μl of plasma, the mixture was stirred, left at room temperature for 10 minutes, and then centrifuged at 3000 rpm for 10 minutes to obtain 25 μl of the supernatant. Then, 750 μl of the enzyme solution was added to the supernatant, and the mixture was stirred. Thereafter, the sample was heated in a water bath at 37° C. for 5 minutes with a standard solution having an HDL cholesterol content of 0, 10, 20, 30, 40 and 50 ml/dl, respectively, and the absorbance at 500 nm was measured and quantified by colorimetry.

In addition, the atherogenic index of plasma was calculated by the following equation.

$$\text{Atherogenic index} = (\text{total cholesterol} - \text{HDL cholesterol})/\text{HDL cholesterol}$$

Figure 12:
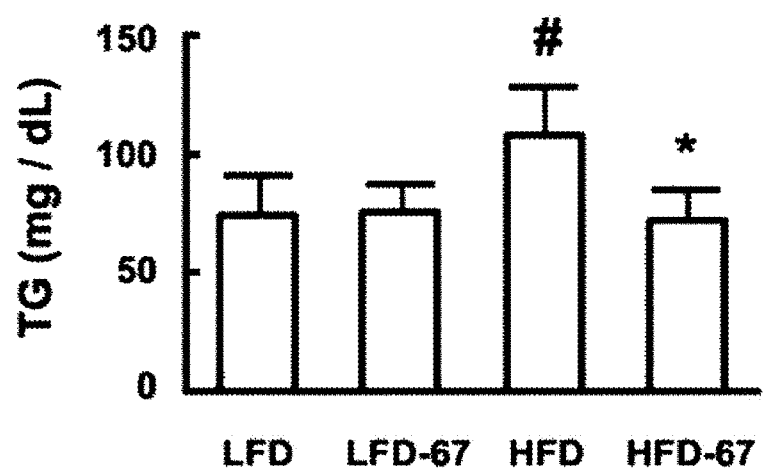
FIG. 12 illustrates the results of measurement of plasma total triglyceride content by experimental group.
Figure 13:
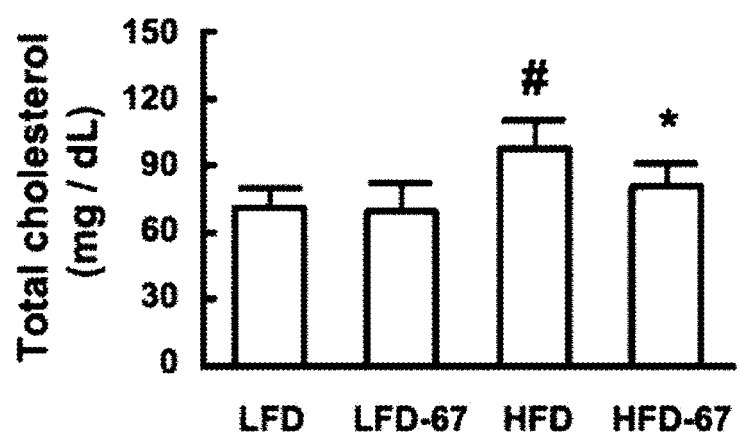
FIG. 13 illustrates the results of measurement of total cholesterol content by experimental group.
Figure 14:
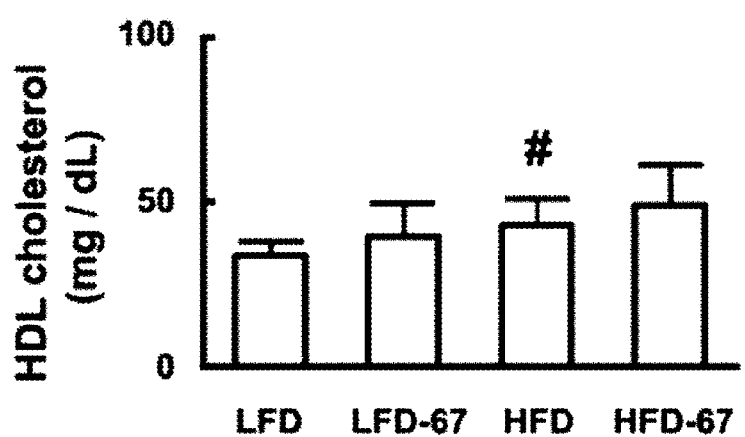
FIG. 14 illustrates the results of HDL cholesterol content measurement by experimental group.
Figure 15:
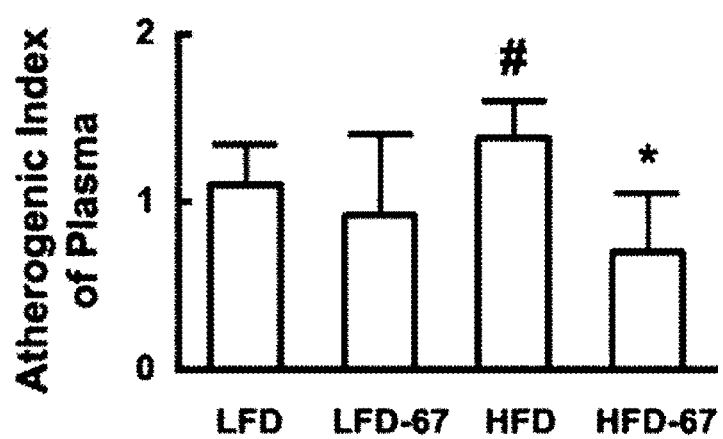
FIG. 15 illustrates the results of measurement of arteriosclerosis index by experimental groups.

FIG. 12 illustrates the results of measurement of plasma total triglyceride content by experimental group, FIG. 13 illustrates the results of measurement of total cholesterol content by experimental group, FIG. 14 illustrates the results of HDL cholesterol content measurement by experimental group, FIG. 15 illustrates the results of measurement of arteriosclerosis index by experimental groups. As illustrated in FIGS. 12 to 15, in the group to which *Lactobacillus sakei* OK67 strain was orally administered together with the high-fat diet after induction of obesity, the plasma triglyceride, plasma total cholesterol content and atherogenic index were significantly reduced compared with the group fed only with high-fat diets after induction of obesity, and HDL cholesterol content was increased.

(4) Analysis of Protein Level Change Related to Lipid Metabolism

In order to investigate the effect of high-fat diet feeding and the administration of *Lactobacillus sakei* OK67 on the protein level change related to lipid metabolism, the levels of PPARγ, C/EBPα, FAS and αFABP, which are the adipocyte differentiation factors, and the levels of macrophage markers TNF-α, IL-1β, F4/80 and CD68 in epididymal adipose tissue of experimental animals were measured by Western blotting.

Figure 16:
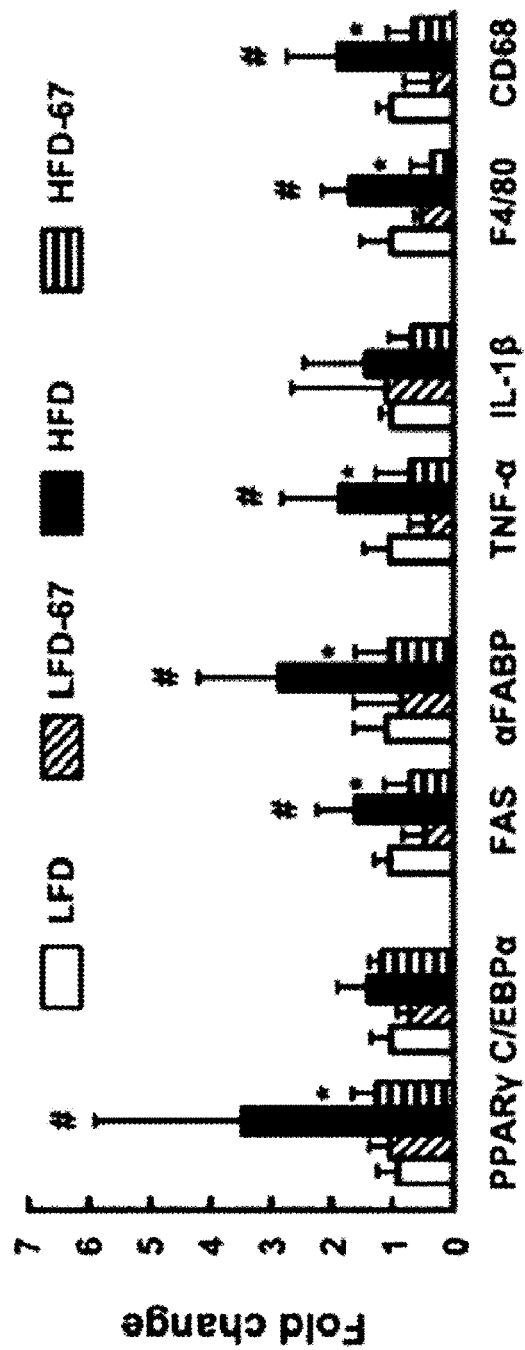
FIG. 16 is a graph illustrating the effect of *Lactobacillus sakei* OK67 on the change of lipid metabolism-related protein level of a model animal in which obesity was induced by a high-fat diet by experimental groups.

Specifically, the epididymal adipose tissue of the experimental animals was homogenized using an RIPA buffer (50 mM Tris-HCl, pH 7.4, 1% NP-40, 0.25% Na-deoxycholate, 150 mM NaCl, 1 mM EDTA) to which protease inhibitor tablet (Roche, USA), phosphatase inhibitor (Roche) and phenylmethanesulfonylfluoride (PMSF) are added, and then centrifuged at 14,000 rpm for 15 minutes to obtain a supernatant. Proteins were isolated from the supernatant by performing 10% SDS-PAGE (sodium dodecyl sulfate-polyacrylamide gel electrophoresis). The isolated protein samples were transferred to a PVDF membrane (Millipore, USA). Thereafter, the sample-transferred PVDF membrane was blocked with 5% skim milk (Difco, France) for 1 hour and 30 minutes in a TBS-T buffer. Then, the primary antibody (Cell Signaling) to PPARγ (peroxisome proliferator-activated receptor-γ), C/EBPα (CCAAT/enhancer-binding protein-α), FAS (fatty acid synthase), αFABP, TNF-α, IL-1β, F4/80, CD68 was added and allowed to react overnight with shaking maintained. Thereafter, after sufficiently washing with TBS-T buffer, the secondary antibody, which is goat anti-rabbit IgG (H+L)-HRP conjugate (BIORAD) was diluted at a ratio of 1:5000 and reacted for 1 hour and 30 minutes. Thereafter, after sufficiently washing with TBS-T buffer and reacting with ECL solution (Clarity western ECL substrate, BIORAD), proteins were detected by chemiluminescence (CLINX science instruments, USA). The density of each band was quantified and the amount of protein expression in the other experimental groups was relatively calculated based on the amount of protein expression in the group fed only with low-fat diets. FIG. 16 is a graph illustrating the effect of *Lactobacillus sakei* OK67 on the change of lipid metabolism-related protein level of a model animal in which obesity was induced by a high-fat diet by experimental groups. As illustrated in FIG. 16, adipocyte differentiation factors and macrophage markers in the epididymal adipose tissue of experimental animals were significantly increased by high-fat diet, but they were significantly decreased by administration of *Lactobacillus sakei* OK67.

Figure 17:
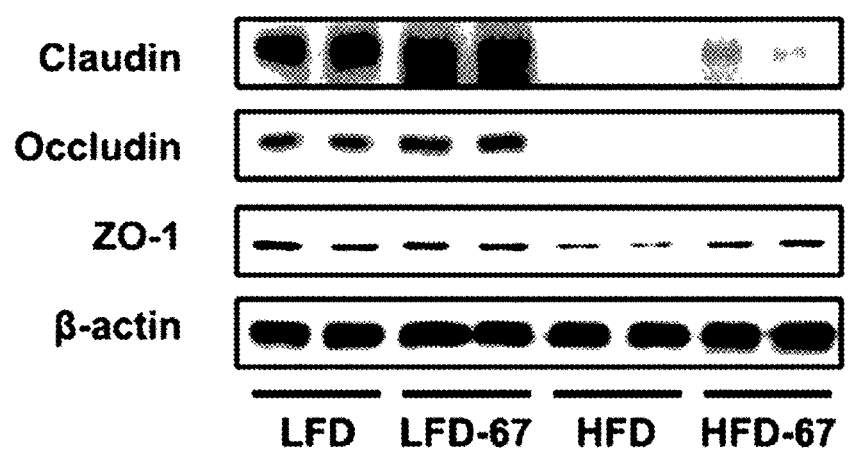
FIG. 17 illustrates the results of analysis of the effect of *Lactobacillus sakei* OK67 on tight junction protein expression in the colon of a model animal in which obesity was induced by a high-fat diet.

(5) Analysis of expression level of tight junction protein in colon Expression levels of tight junction proteins in colon tissues of sacrificed experimental animals were analyzed by immunoblotting. Specifically, the colon tissues of sacrificed experimental animals were homogenized in lysis buffer and then subjected to SDS 10% (w/v) polyacrylamide gel electrophoresis to isolate whole protein samples. Thereafter, the entire protein sample was transferred to a polyvinylidene difluoride membrane. Thereafter, the entire protein sample transferred to the membrane was reacted with ZO-1, occludin, claudin-1 and β-actin primary antibody (diluted at a ratio of 1:1000) overnight at 4° C. Thereafter, the entire protein sample was reacted with an anti-mouse immunoglobulin G secondary antibody (Santa Cruz Biotechnology, USA; diluted at a ratio of 1:2000) for 1 hour at room temperature. Thereafter, the sample was washed with PBS containing 0.1% Tween 20 three times for 10 minutes each, and developed after fluorescence color development. FIG. 17 illustrates the results of analysis of the effect of *Lactobacillus sakei* OK67 on tight junction protein expression in the colon of a model animal in which obesity was induced by a high-fat diet. As illustrated in FIG. 17, the high-fat diet caused a decrease in expression of ZO-1, occludin, claudin-1 which are tight junction proteins. On the other hand, *Lactobacillus sakei* OK67 effectively inhibited the decrease of the expression of the tight junction protein caused by the high-fat diet.

The *Lactobacillus sakei* OK67 strain inhibits endotoxin production in the intestinal microorganism and induces tight junction protein expression in the colon to mitigate glucose intolerance and obesity induced by high-fat diets.

6. In-Vivo Experiments on the Anti-Inflammatory Effects of Lactic Acid Bacteria (1) Experimental Method In order to investigate the effect of *Lactobacillus sakei* OK67 strain on the arthritis-induced model animals, a total of 28 mice of 8-week-old male DBA/1J were divided into four groups (NOR, AC, AO, AI) of 7 mice each. Bovine type II collagen was used as an immunogen to induce arthritis in the remaining groups of AC group, AO group and AI group except the normal NOR group. Specifically, 100 μg of a collagen immunogen was injected intradermally into the proximal portion of the mouse tail, and primary immunization was performed. On the 21st day after the primary immunization, the same amount of collagen immunogen was injected intradermally and secondarily immunized in the same manner. At this time, bovine type II collagen was dissolved in 0.05 M acetic acid as a collagen immunogen and the same amount of Freund's Complete Adjuvant was added to emulsify the bovine type II collagen.

From the next day after the secondary immunization, NOR group and AC group were orally administered vehicle (50 mM sodium bicarbonate buffer containing 1% glucose) daily for 20 days. In AO group, *Lactobacillus sakei* OK67 strain 1×10$^9$ CFU was suspended in 0.1 ml of a vehicle (50 mM sodium bicarbonate buffer containing 1% glucose) and orally administered daily for 20 days. In AI group, ibuprofen was suspended in a vehicle (50 mM sodium bicarbonate buffer containing 1% glucose) and orally administered daily in a volume of 50 mg/kg weight, and the experiment was terminated the next day.

(2) Analysis Method

Arthritis severity and arthritis incidence of paws were measured from the stage of arthritis induction.

The paws and vicinity of paws were observed with the naked eyes to assess arthritis severity of paws step by step by a macroscopic score according to the criteria in Table 3 below (Arii et al., 2008). The highest macroscopic score that may be given to each mouse is 16.

TABLE 3

| Step | Observation of appearance |
|---|---|
| 0 | normal |
| 1 | focal slight swelling and/or redness in one digit |
| 2 | moderate swelling and erythema |

TABLE 3-continued

| Step | Observation of appearance |
|---|---|
| 3 | marked swelling and erythema of the limb |
| 4 | maximal swelling, erythema, deformity, and/or ankylosis |

The volume increase of paws, myeloperoxidase (MPO) activity of the paw joint tissues, and tissue microscopic analysis were performed after the end of the experiment.

At the end of the experiment, the experimental animals were sacrificed and paw joint tissue was collected and immediately frozen at −70° C. and used as a sample. The myeloperoxidase (WO) activity in the paw joint tissue was measured using the Mouse MPO assay ELISA kit (Hbt HK210, USA). In addition, for tissue microscopic analysis, paw joint tissue was fixed with 4% paraformaldehyde, dried, embedded with paraffin, cut to a thickness of 20 μm. After staining with either hematoxylin-eosin, toluidine blue or safranin 0, the appearance of the tissue was microscopically evaluated.

In addition, paw joint tissue was homogenized in radio-immunoprecipitation assay (RIPA) lysis buffer, and SDS 10% (w/v) polyacrylamide gel electrophoresis was performed to isolate the entire protein sample. The entire protein sample was then transferred to a polyvinylidene difluoride membrane. Thereafter, the entire protein sample transferred to the membrane was reacted with COX-2, iNOS, p65, p-p65, p38, p-p38, JNK, p-JNK, ERK, p-ERK, TAK1, p-TAK1 and β-actin primary antibody (diluted at a ratio of 1:1000) overnight at 4° C. Thereafter, the entire protein sample was reacted with an anti-mouse immunoglobulin G secondary antibody (Santa Cruz Biotechnology, USA; diluted at a ratio of 1:2000) for 1 hour at room temperature. Thereafter, the sample was washed with PBS containing 0.1% Tween 20 three times for 10 minutes each, and developed after fluorescence color development.

In addition, the experimental animals were sacrificed at the end of the experiment and the spleen was aseptically collected. Thereafter, the spleen was ground to prepare single cell suspension, and cells were dissolved in Tris-buffered ammonium chloride, and then suspended in RPMI 1640 medium. Thereafter, T cells were isolated by using Pan T cell isolation kit II (Miltenyi Biotec, Bergisch Gladbach, Germany). The isolated T cells were stained with an anti-FoxP3 or anti-IL-17A antibody and the distribution of Th17 cells and Treg cells was analyzed by using a fluorescence-activated cell sorting (FACS) device (C6 Flow Cytometer® System, San Jose, Calif., USA). In addition, splenic T cell differentiation markers were analyzed using qRT-PCR.

In addition, expression levels of inflammatory cytokines, anti-inflammatory cytokines, prostaglandin E2 ($PGE_2$), and NO in the paw joint tissue were analyzed using an ELISA kit. Specifically, paw joint tissue was homogenized in a radio immunoprecipitation assay (RIPA) lysis buffer containing 0.1% protease inhibitor cocktail and 1% phosphatase inhibitor cocktail. Thereafter, the tissue homogenate was centrifuged to obtain a supernatant. The resulting supernatant was transferred to a 96-well plate and the concentrations of TNF-α, IL-1β, IL-10, IL-17 and PGE2 were measured using an ELISA kit.

(3) Experiment Result

Figure 18:
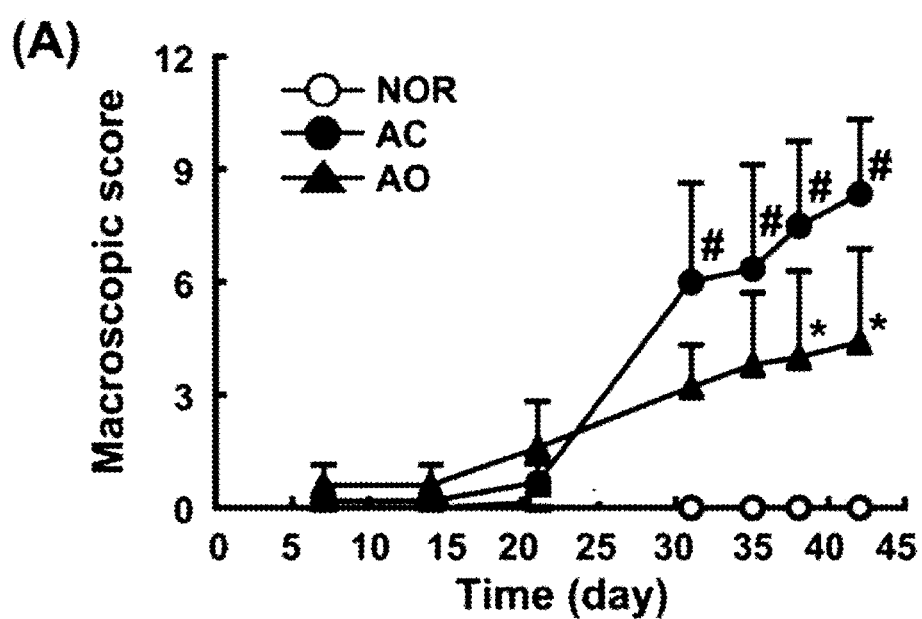
FIG. 18 is a graph illustrating the effect of *Lactobacillus sakei* OK67 strain on arthritis severity in a model animal experiment in which arthritis was induced by collagen.
Figure 19:
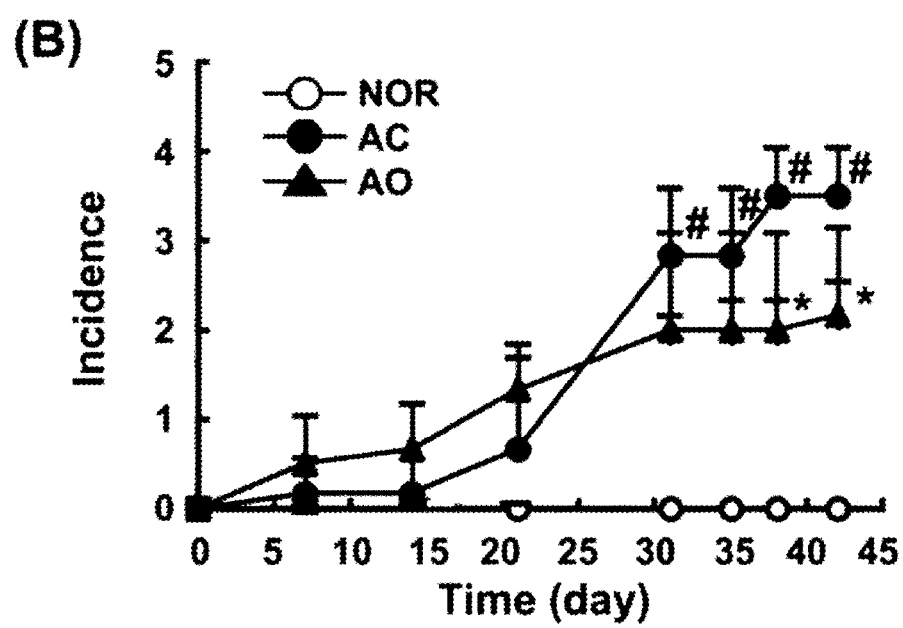
FIG. 19 is a graph illustrating the effect of *Lactobacillus sakei* OK67 strain on arthritis incidence in a model animal experiment in which arthritis was induced by collagen.
Figure 20:
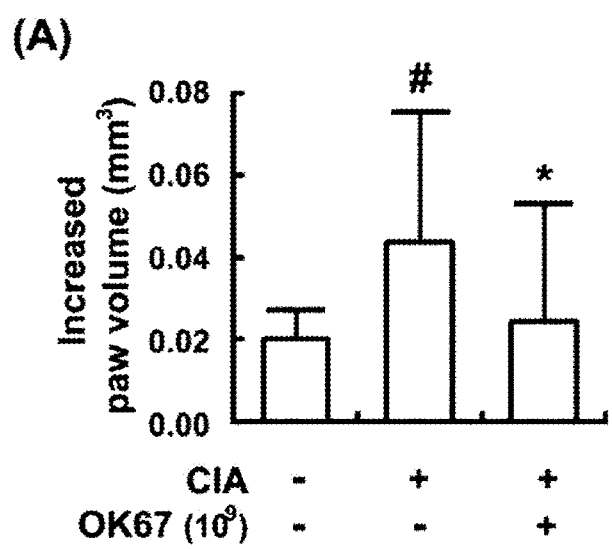
FIG. 20 is a graph illustrating the effect of *Lactobacillus sakei* OK67 strain on the volume increase of the paw in a model animal experiment in which arthritis was induced by collagen.
Figure 21:
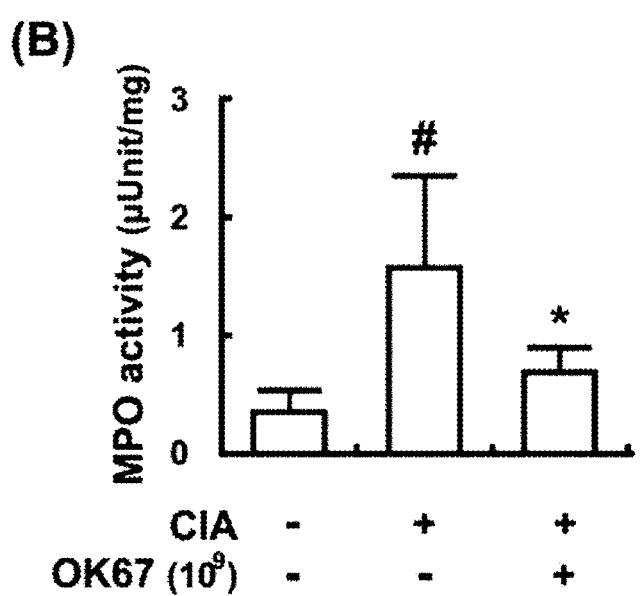
FIG. 21 is a graph illustrating the effect of *Lactobacillus sakei* OK67 strain on the activity of myeloperoxidase (MPO) in paw joint tissues in a model animal experiment in which arthritis was induced by collagen.
Figure 22:
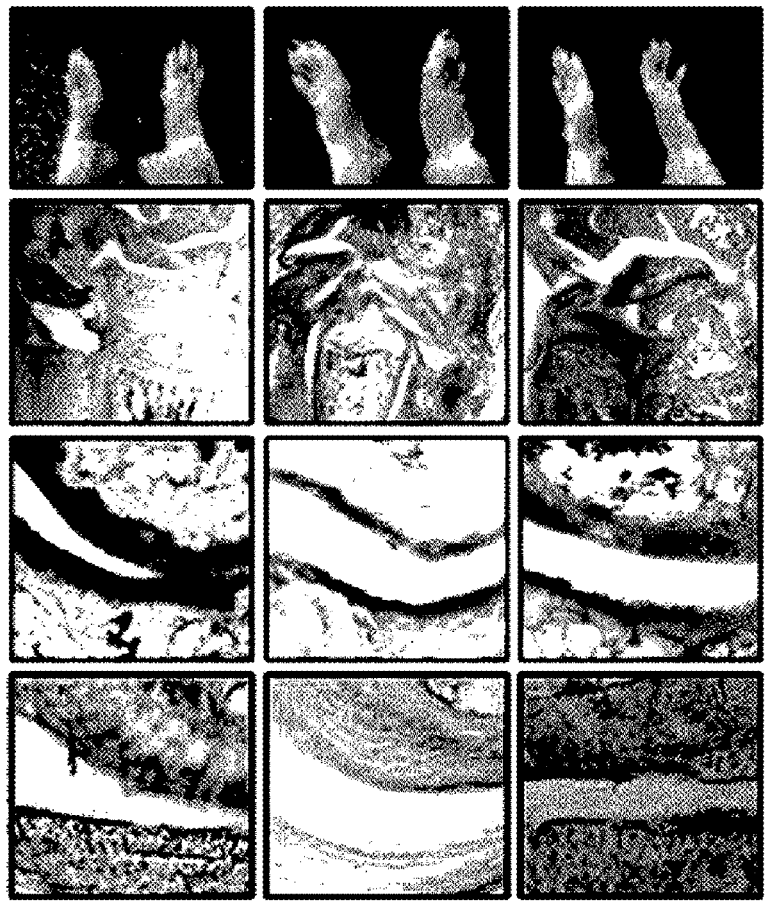
FIG. 22 is a photograph illustrating the effect of *Lactobacillus sakei* OK67 strain on micro-appearance of paw joint tissues in a model animal experiment in which arthritis was induced by collagen.

FIG. 18 is a graph illustrating the effect of *Lactobacillus sakei* OK67 strain on arthritis severity in a model animal experiment in which arthritis was induced by collagen. In addition, FIG. 19 is a graph illustrating the effect of *Lactobacillus sakei* OK67 strain on arthritis incidence in a model animal experiment in which arthritis was induced by collagen. In addition, FIG. 20 is a graph illustrating the effect of *Lactobacillus sakei* OK67 strain on the volume increase of the paw in a model animal experiment in which arthritis was induced by collagen. In addition, FIG. 21 is a graph illustrating the effect of *Lactobacillus sakei* OK67 strain on the activity of Myeloperoxidase (MPO) in paw joint tissues in a model animal experiment in which arthritis was induced by collagen. In addition, FIG. 22 is a photograph illustrating the effect of *Lactobacillus sakei* OK67 strain on micro-appearance of paw joint tissues in a model animal experiment in which arthritis was induced by collagen.

As illustrated in FIGS. 18 to 22, *Lactobacillus sakei* OK67 strain exhibited high anti-inflammatory efficacy and exhibited very superior improvement or therapeutic effect on arthritis.

Figure 23:
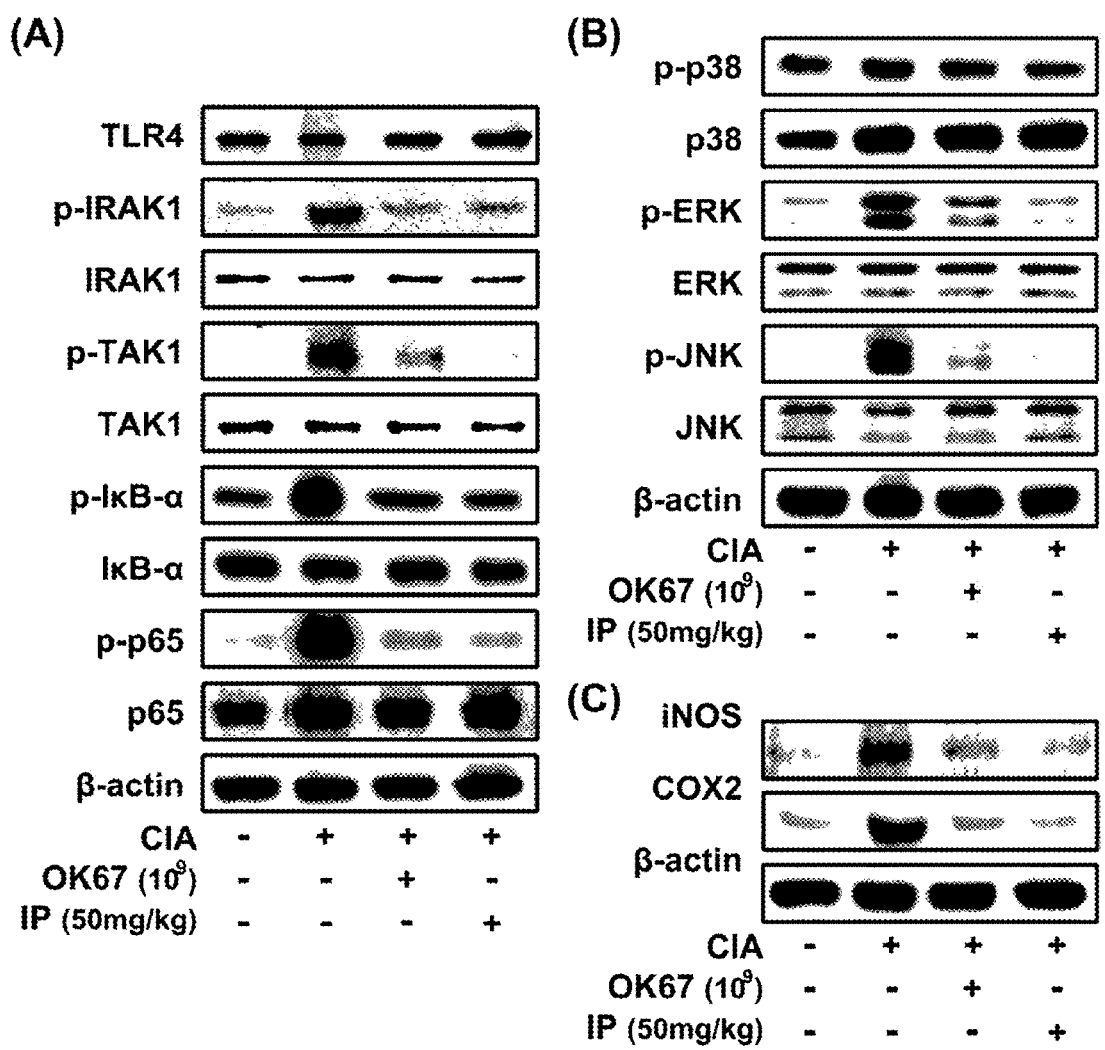
FIG. 23 is a photograph illustrating the effect of *Lactobacillus sakei* OK67 strain on the expression of iNOS and COX-2 in the paw joint tissue and the expression of signal transduction pathway elements such as NF-κB and MAPKs in a model animal experiment in which arthritis was induced by collagen.

FIG. 23 is a photograph illustrating the effect of *Lactobacillus sakei* OK67 strain on the expression of iNOS and COX-2 in the paw joint tissue and the expression of signal transduction pathway elements such as NF-κB and MAPKs in a model animal experiment in which arthritis was induced by collagen. As illustrated in FIG. 23, the treatment of collagen significantly increased the expression of iNOS and COX-2, the phosphorylation of IRAK1, TAK1 and IκB-α, and the activation of NF-κB and MAPKs (ERK, JNK, and p38). On the other hand, *Lactobacillus sakei* OK67 strain inhibited both the expression of iNOS and COX-2 and the phosphorylation of IRAK1, TAK1 and IκB-α, and the activation of NF-κB and MAPKs (ERK, JNK, and p38).

Figure 24:
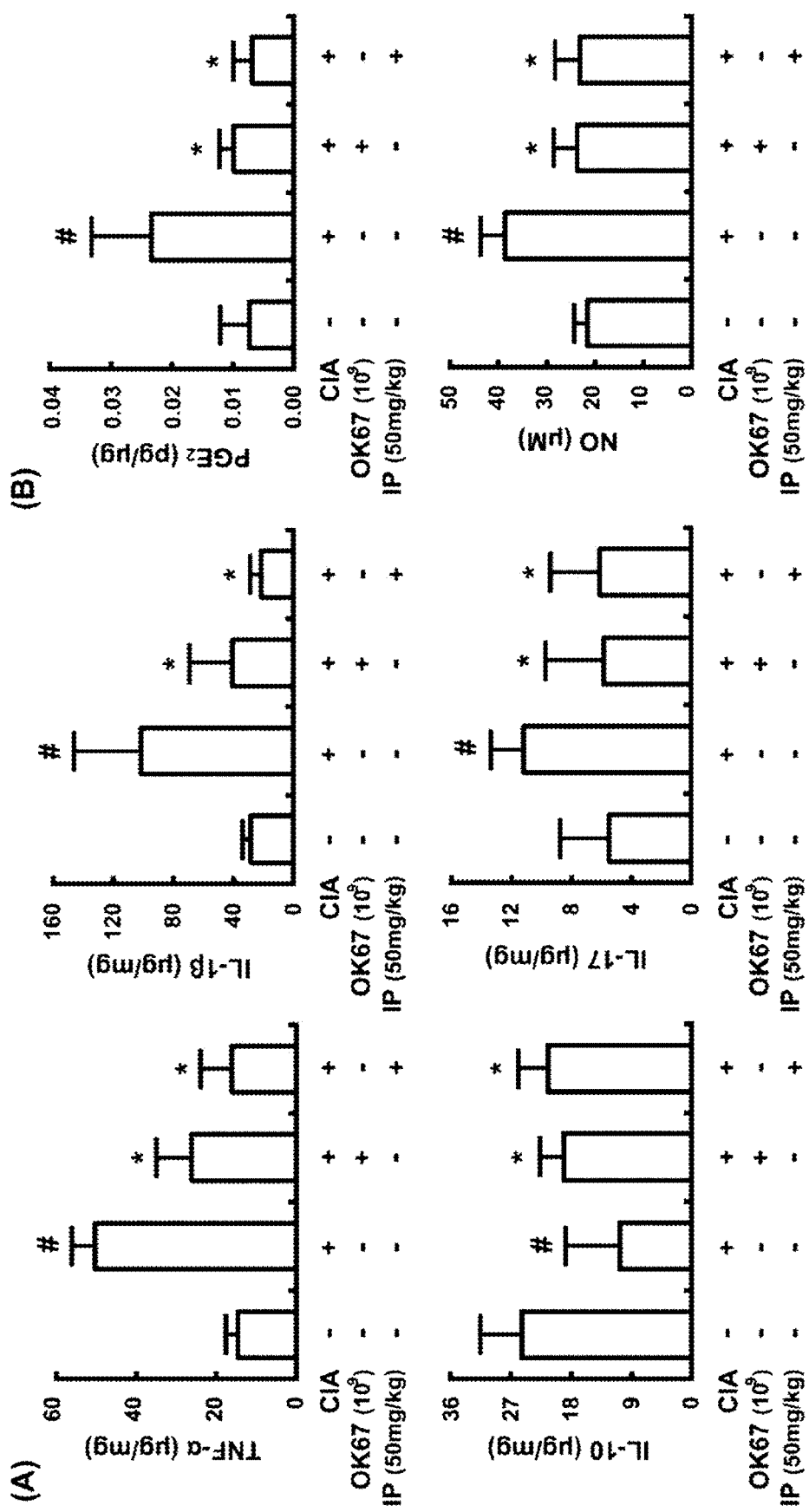
FIG. 24 is a graph illustrating the effect of *Lactobacillus sakei* OK67 strain of the expression of inflammatory cytokines and anti-inflammatory cytokines in paw joint tissues and the production of prostaglandin E2 (PGE$_2$) and NO in a model animal experiment in which arthritis was induced by collagen.

FIG. 24 is a graph illustrating the effect of *Lactobacillus sakei* OK67 strain on the expression of inflammatory cytokines and anti-inflammatory cytokines in paw joint tissues and the production of prostaglandin E2 ($PGE_2$) and NO in a model animal experiment in which arthritis was induced by collagen. As illustrated in FIG. 24, the treatment of collagen significantly increased the production of NO and PGE2, while *Lactobacillus sakei* OK67 strain inhibited NO and PGE2 production to levels of 89% and 86%, respectively. In addition, the treatment of collagen increased the expression of inflammatory cytokines (TNF-α, IL-1β and IL-17a) and inhibited the expression of anti-inflammatory cytokines (IL-10), while *Lactobacillus sakei* OK67 strain inhibited the expression of inflammatory cytokines (TNF-α, IL-1β and IL-17a) and induced the expression of anti-inflammatory cytokines (IL-10).

Figure 25:
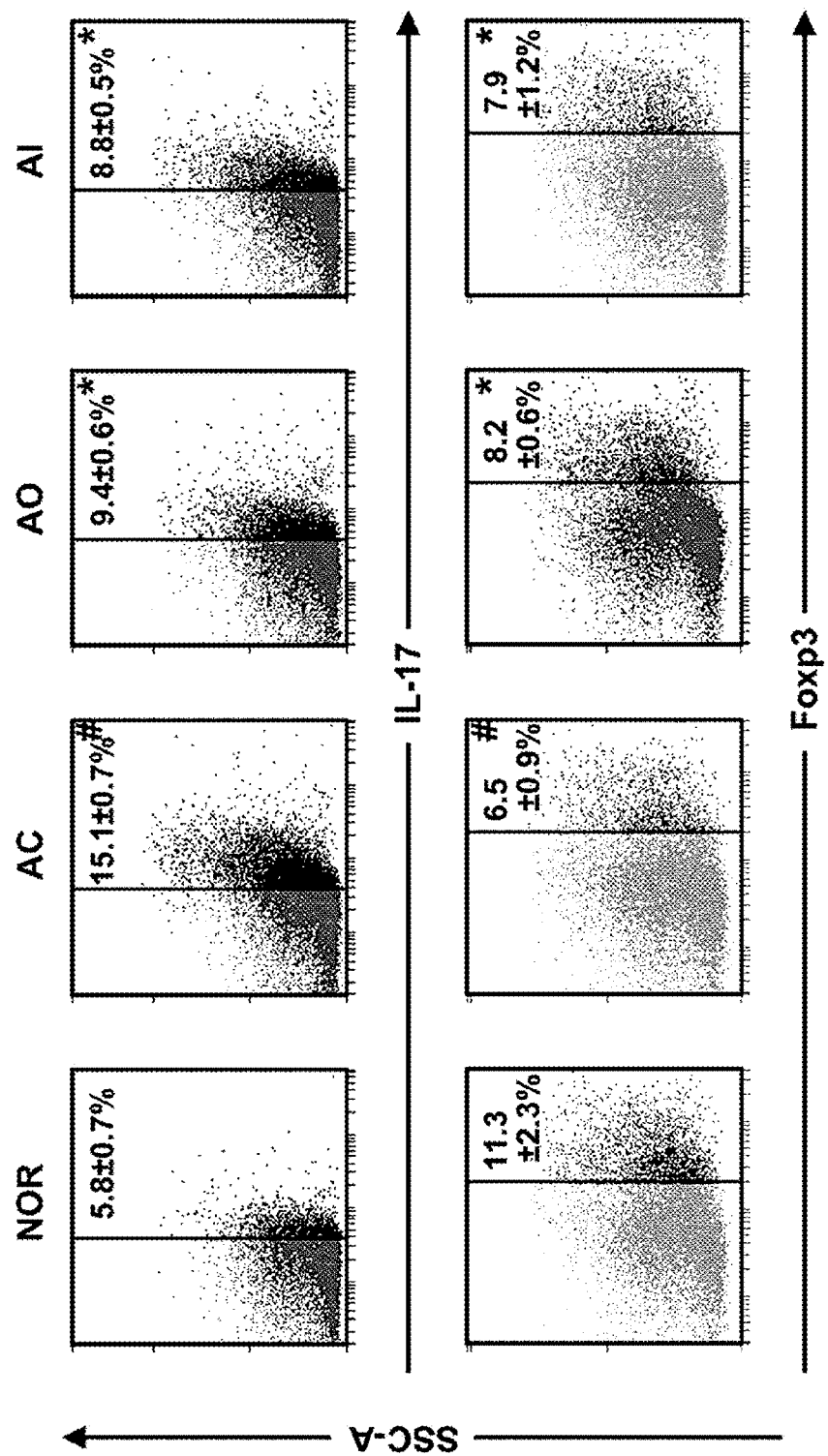
FIG. 25 illustrates the effect of *Lactobacillus sakei* OK67 strain on splenic T cell differentiation in a model animal experiment in which arthritis was induced by collagen.
Figure 26:
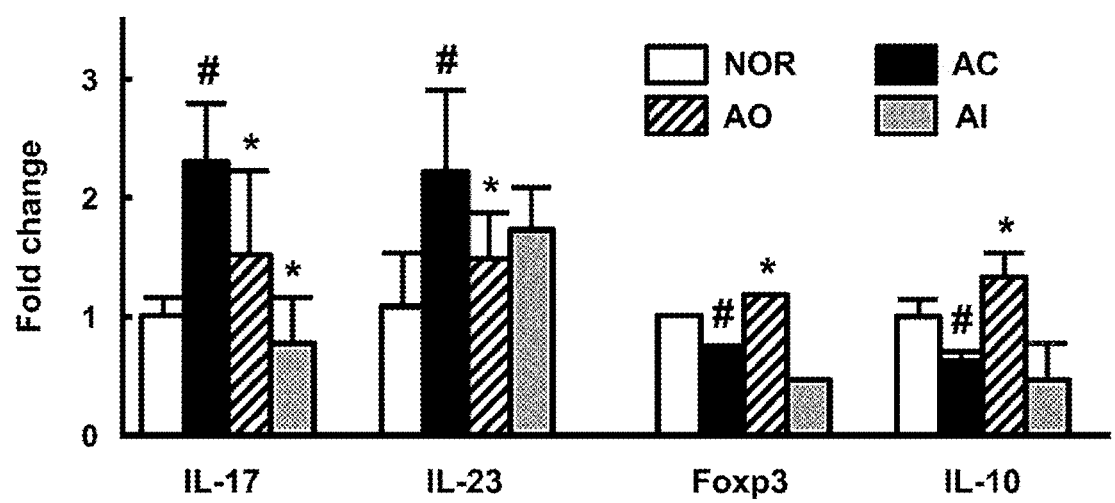
FIG. 26 illustrates the effect of *Lactobacillus sakei* OK67 strain on splenic T-cell differentiation markers in a model animal experiment in which arthritis was induced by collagen.

FIG. 25 illustrates the effect of *Lactobacillus sakei* OK67 strain on splenic T cell differentiation in a model animal experiment in which arthritis was induced by collagen. In addition, FIG. 26 illustrates the effect of *Lactobacillus sakei* OK67 strain on splenic T-cell differentiation markers in a model animal experiment in which arthritis was induced by collagen. As illustrated in FIG. 25, the treatment of collagen significantly increased the differentiation of T cells into Th17 cells (T helper 17 cells) and inhibited the differentiation into Treg cells. On the other hand, *Lactobacillus sakei* OK67 strain inhibited the differentiation of T cells into Th17 cells (T helper 17 cells) and promoted the differentiation into Treg cells. In addition, as illustrated in FIG. 26, the treatment of collagen significantly induced IL-17 and IL-23 expression and inhibited Foxp3 expression. On the other hand, *Lactobacillus sakei* OK67 strain inhibited the expression of IL-17 and increased Foxp3 expression.

*Lactobacillus sakei* OK67 strain inhibited the differentiation of collagen-induced T cells into Th17 cells (T helper 17 cells) and increased the differentiation of collagen-inhibited T cells into Treg cells. In addition, *Lactobacillus sakei* OK67 strain inhibited the expression of collagen-induced TNF-α, IL-1β, IL-6 and IL-17 and the activation of NF-κB and MAPKs (p38, JNK, ERK). On the other hand, *Lactobacillus sakei* OK67 strain induced IL-10 expression. Based on these results, the *Lactobacillus sakei* OK67 strain inhibits the activation of NF-κB and restores the balance of Th17/Treg cells, thereby alleviating inflammatory diseases such as colitis and arthritis or immune diseases. In addition, the *Lactobacillus sakei* OK67 strain restores the balance of Th17/Treg cells and regulates immunity, thereby alleviating immunological diseases such as rheumatoid arthritis and allergies, and may also enhance weakened immunity.

7. Effectiveness Evaluation of Alcohol-Induced Gastric Ulcer Improvement in Lactic Acid Bacteria (In Vivo)

(1) Experimental Animals

Five-week-old ICR male mice were purchased from Raon Biotech Co. and raised for one week under controlled environmental conditions in which humidity was 50±10%, temperature was 25±2° C., and lighting was repeatedly turned on for 12 hours and turned off for 12 hours, and then were used for experiments. The mice were fed with standard laboratory feed (Samyang, Korea) as feeds, and were allowed to drink water freely. In all experiments, six mice were used in one group.

(2) Induction of Gastric Ulcer by Alcohol and Sample Administration

In one experimental group, *Lactobacillus sakei* OK67 was suspended in physiological saline and was orally administered for three days in an amount of $1 \times 10^9$ CFU once a day, and in a positive control group, ranitidine, a commercial gastric ulcer treatment, was orally administered for three days in an amount of 50 mg/kg once a day. In addition, in the normal group and the negative control group, physiological saline was orally administered for three days in an amount of 0.1 ml once a day. Samples or physiological saline were orally administered for 3 days, and then the experimental mice were not allowed to eat food and drink water for 18 hours. On the 4th day of the experiment, 1 hour after the administration of the sample or the physiological saline, 0.2 ml of 99% pure ethanol was orally administered to all experimental mice except the normal group to induce gastric ulcer. In addition, in the normal group, 0.2 ml of physiological saline was orally administered instead of ethanol.

(3) Measurement of Macroscopic Indicators Related to Gastric Damage

After 3 hours of ethanol administration, the experimental mice were sacrificed and the stomach tissue was removed. The stomach was cut in a longitudinal direction and washed with a phosphate buffered saline (PBS) solution. The degree of gastric damage was visually or microscopically examined and scored according to the degree of damage (reference document: Park, S. W., Oh, T. Y., Kim, Y. S., Sim, H., et al., *Artemisia asiatica* extracts protect against ethanol-induced injury in gastric mucosa of rats. J. Gastroenterol. Hepatol. 2008, 23, 976?984).

(4) Measurement of Activity of Myeloperoxidase (MPO)

200 μl of 10 mM potassium phosphate buffer (pH 7.0) containing 0.5% hexadecyl trimethyl ammonium bromide was homogenized in 100 mg of stomach tissue. Then, the supernatant was obtained by centrifugation for 10 minutes under the condition of 4° C. and 10,000×g. 50 μl of the supernatant was added to 0.95 ml of reaction solution (containing 1.6 mM tetramethyl benzidine and 0.1 mM $H_2O_2$) and the absorbance was microscopically measured at 650 nm with the reaction at 37° C. Myeloperoxidase (WO) activity was calculated using peroxide 1 μmol/ml as 1 unit produced as a reactant.

(5) Measurement of Inflammation Index

The stomach tissue was purified with Qiagen RNeasy Mini Kit, 2 μg of mRNA was isolated, and cDNA was prepared using Takara Prime Script Rtase. Thereafter, the expression levels of CXCL4 [chemokine (C—X—C motif) ligand 4], TNF-α (tumor necrosis factor-alpha) and IFN-γ were measuring using quantitative real time polymerase chain reaction (Qiagn thermal cycler, Takara SYBER premix agent, Thermal cycling conditions: activation of DNA polymerase for 5 min at 95° C., followed by 40 cycles of amplification for 10 s at 95° C. and for 45 s at 60° C.). Table 4 below shows the primer sequences used for the quantitative real time polymerase chain reaction as per the cytokines to be analyzed.

TABLE 4

| Cytokines to be analyzed | Type of primer | Primer nucleotide sequence |
|---|---|---|
| TNF-α | Forward | 5'-CTGTAGCCCACGTCGTAGC-3' |
| | Reverse | 5'-TTGAGATCCATGCCGTTG-3' |
| CXCL4 | Forward | 5'-AGTCCTGAGCTGCTGCTTCT-3' |
| | Reverse | 5'-GATCTCCATCGCTTTCTTCG-3' |
| IFN-γ | Forward | 5'-TCAAGTGGCATAGATGTGGAAGAA-3' |
| | Reverse | 5'-TGGCTCTGCAGGATTTTCATG-3' |

(6) Experimental Results

Figure 27:
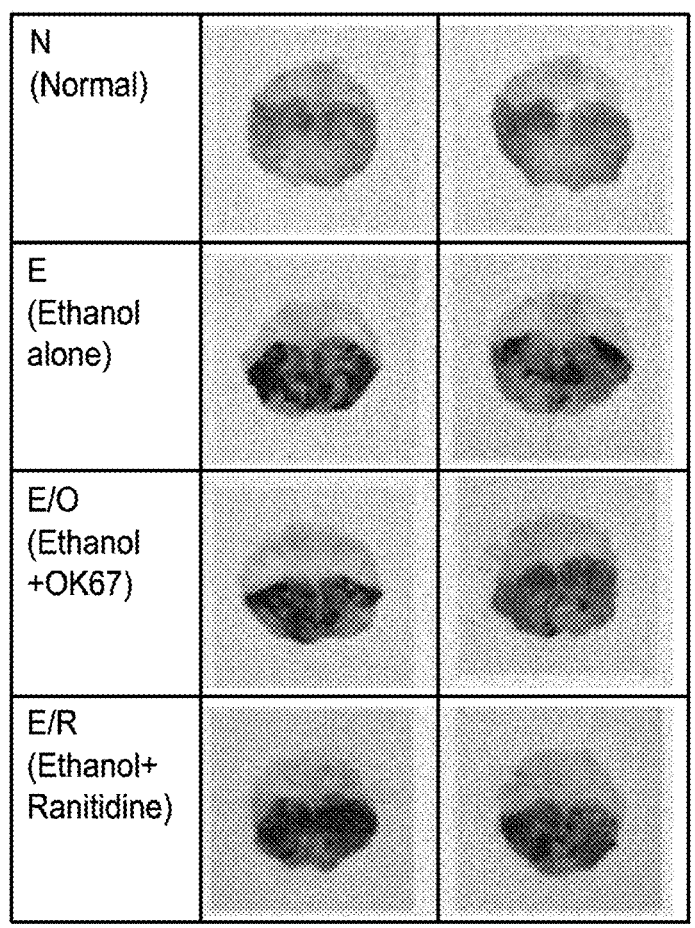
FIG. 27 is a photograph illustrating the effect of *Lactobacillus sakei* OK67 strain on the stomach mucosa of a mouse induced by gastric ulcer caused by ethanol.
Figure 28:
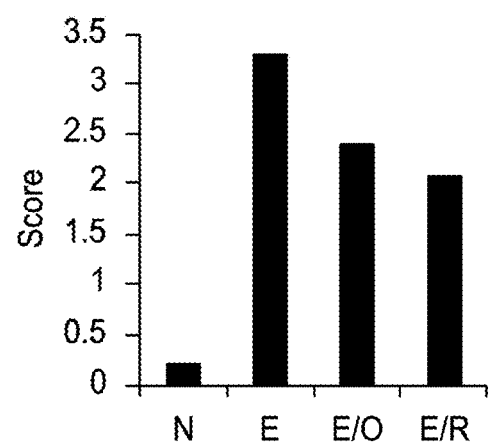
FIG. 28 is a graph illustrating the effect of *Lactobacillus sakei* OK67 strain on the stomach mucosa of a mouse induced by gastric ulcer caused by ethanol by the gross gastric lesion score.
Figure 29:
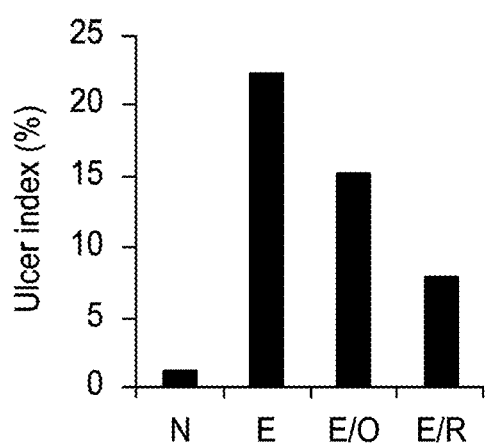
FIG. 29 is a graph illustrating the effect of *Lactobacillus sakei* OK67 strain on the stomach mucosa of a mouse induced by gastric ulcer caused by ethanol by the ulcer index.
Figure 30:
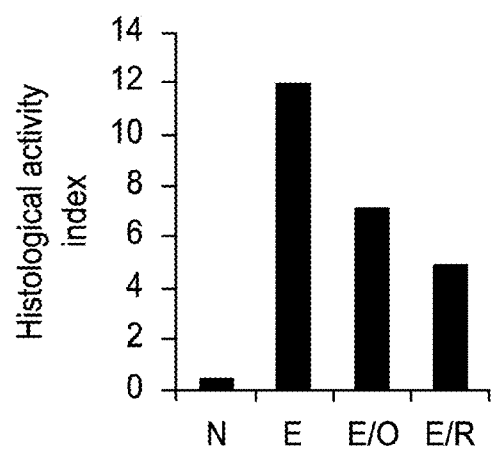
FIG. 30 is a graph illustrating the effect of *Lactobacillus sakei* OK67 strain on the stomach mucosa of a mouse induced by gastric ulcer caused by ethanol by Histological activity index.
Figure 31:
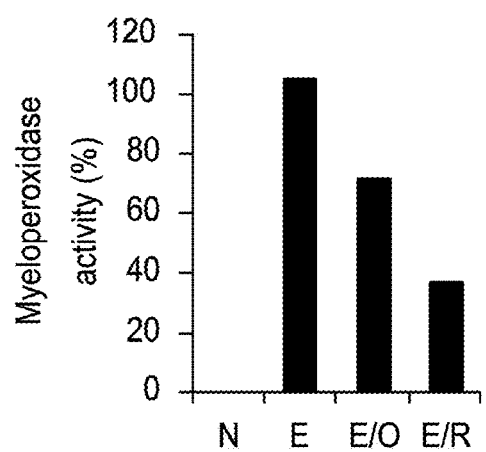
FIG. 31 is a graph illustrating the effect of *Lactobacillus sakei* OK67 strain on the stomach mucosa of a mouse induced by gastric ulcer caused by ethanol by myeloperoxidase (MPO) activity.
Figure 32:
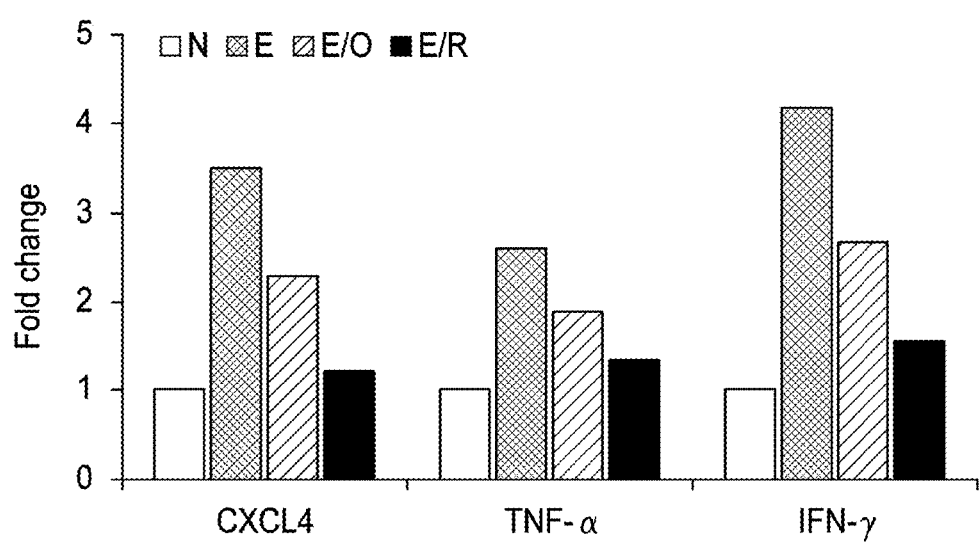
FIG. 32 is a graph illustrating the effect of *Lactobacillus sakei* OK67 strain on the stomach mucosa of a mouse induced by gastric ulcer caused by ethanol by the expression levels of CXCL4, TNF-α and IFN-γ.

FIG. 27 is a photograph illustrating the effect of *Lactobacillus sakei* OK67 strain on the stomach mucosa of a mouse induced by gastric ulcer caused by ethanol, FIG. 28 is a graph illustrating the effect of *Lactobacillus sakei* OK67 strain on the stomach mucosa of a mouse induced by gastric ulcer caused by ethanol by the gross gastric lesion score, FIG. 29 is a graph illustrating the effect of *Lactobacillus sakei* OK67 strain on the stomach mucosa of a mouse induced by gastric ulcer caused by ethanol by the ulcer index, and FIG. 30 is a graph illustrating the effect of *Lactobacillus sakei* OK67 strain on the stomach mucosa of a mouse induced by gastric ulcer caused by ethanol by Histological activity index. In addition, FIG. 31 is a graph illustrating the effect of *Lactobacillus sakei* OK67 strain on the stomach mucosa of a mouse induced by gastric ulcer caused by ethanol by myeloperoxidase (MPO) activity. In addition, FIG. 32 is a graph illustrating the effect of *Lactobacillus sakei* OK67 strain on the stomach mucosa of a mouse induced by gastric ulcer caused by ethanol by the expression levels of CXCL4, TNF-α and IFN-γ. In FIG. 32, CXCL4 expression level, TNF-α expression level, and IFN-γ expression level in the experimental groups except the normal group were expressed as a fold change based on the expression level of the normal group. In FIG. 27 to FIG. 32, "N" refers to a normal group, "E" refers to a negative control group in which gastric ulcer is induced by ethanol and physiological saline was administered as a sample, "E/O" refers to an experimental group in which gastric ulcer was induced by ethanol and *Lactobacillus sakei* OK67 was administered as a sample, and "E/R" refers to an experimental group in which gastric ulcer was induced by ethanol and ranitidine was administered as a sample. As illustrated in FIGS. 27 to 31, *Lactobacillus sakei* OK67 effectively alleviated stomach damage or gastric ulcer induced by ethanol. In addition, as illustrated in FIG. 32, *Lactobacillus sakei* OK67 significantly reduced inflammatory index levels in mice in which stomach injury or gastric ulcer was induced by ethanol.

8. Effectiveness Evaluation of Alcohol-Induced Liver Damage Alleviation in Lactic Acid Bacteria (In Vivo)

(1) Experimental Animals

Five-week-old ICR male mice were purchased from Raon Biotech Co. and raised for one week under controlled environmental conditions in which humidity was 50±10%, temperature was 25±2° C., and lighting was repeatedly turned on for 12 hours and turned off for 12 hours, and then were used for experiments. The mice were fed with standard laboratory feed (Samyang, Korea) as feeds, and were allowed to drink water freely. In all experiments, six mice were used in one group.

(2) Induction of Liver Damage by Alcohol and Sample Administration

In one experimental group, *Lactobacillus sakei* OK67 was suspended in physiological saline and was orally administered for three days in an amount of $1 \times 10^9$ CFU once a day, and in a positive control group, silymarin, a commercial liver damage treatment, was orally administered for three days in an amount of 50 mg/kg once a day. In addition, in the normal group and the negative control group, physiological saline was orally administered for three days in an amount of 0.1 ml once a day. Samples or physiological saline were orally administered for 3 days. After 3 hours, ethanol in an amount of 6 ml/kg was intraperitoneally administered to mice in all experimental groups except the normal group to induce liver damage. In addition, physiological saline was intraperitoneally administered to the normal group in an amount of 6 ml/kg in place of ethanol. Thereafter, experimental mice were not allowed to eat food and drink water for 12 hours, and then were sacrificed to perform cardiac blood collection.

(3) Liver Function Indicator Measurement and Result

The collected blood was left at room temperature for 60 minutes and centrifuged at 3,000 rpm for 15 minutes to isolate the serum. Glutamic pyruvate transaminase (GPT) and glutamic oxalacetic transaminase (GOT) of the isolated serum were measured using a blood analysis kit (ALT & AST measurement kit; Asan Pharm. Co., Korea). The results are shown in Table 5 below. As shown in Table 5 below, *Lactobacillus sakei* OK67 effectively improved ethanol-induced liver damage.

TABLE 5

| Experimental Groups | GOT (IU/L) | GPT (IU/L) |
|---|---|---|
| Normal group | 72.5 | 51.2 |
| Negative control group | 147.3 | 199.2 |
| Group administered ethanol and OK67 | 132.5 | 155.2 |
| Group administered ethanol and silymarin | 125.6 | 118.2 |

* OK67: *Lactobacillus sakei* OK67

9. Sequence Analysis of Full Genome of *Lactobacillus sakei* OK67 Strain

Figure 33:
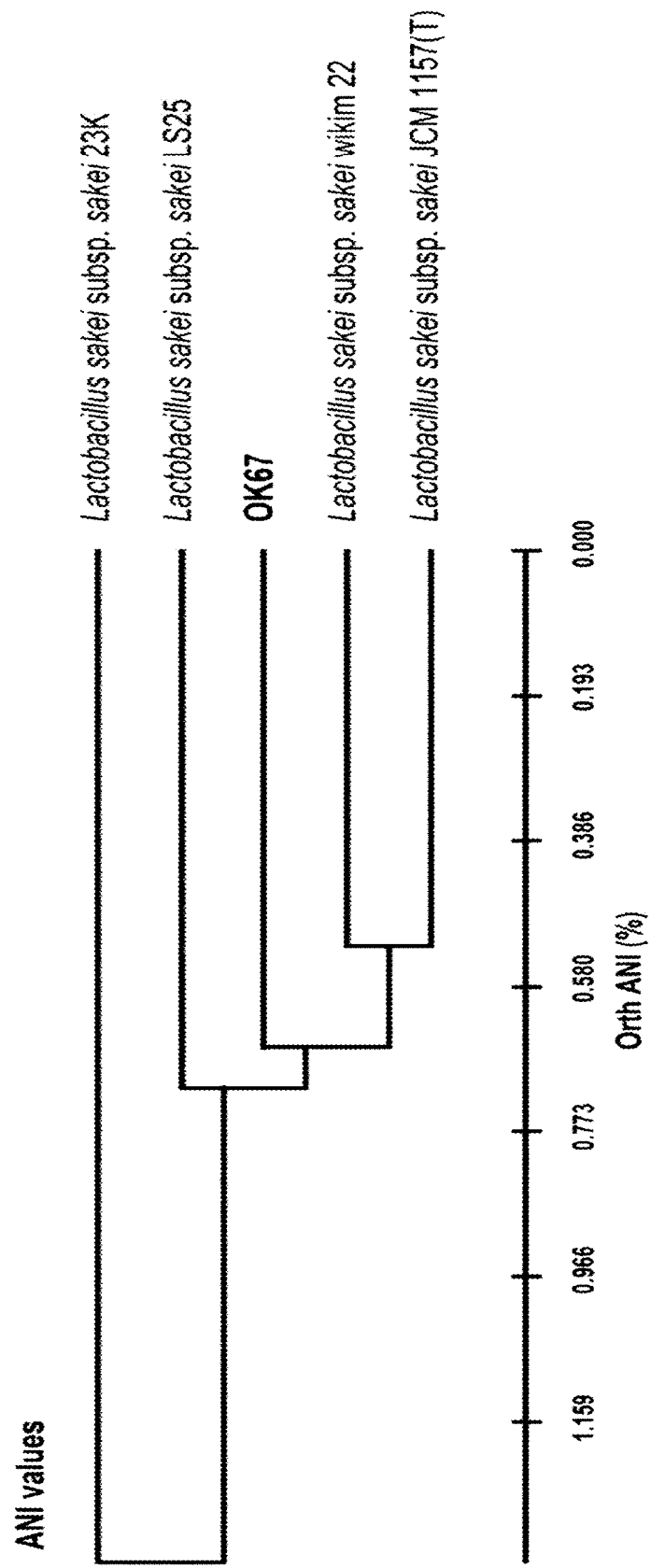
FIG. 33 illustrates a comparison of the average nucleotide identity (ANI) values between strains similar to *Lactobacillus sakei* OK67.
Figure 34:
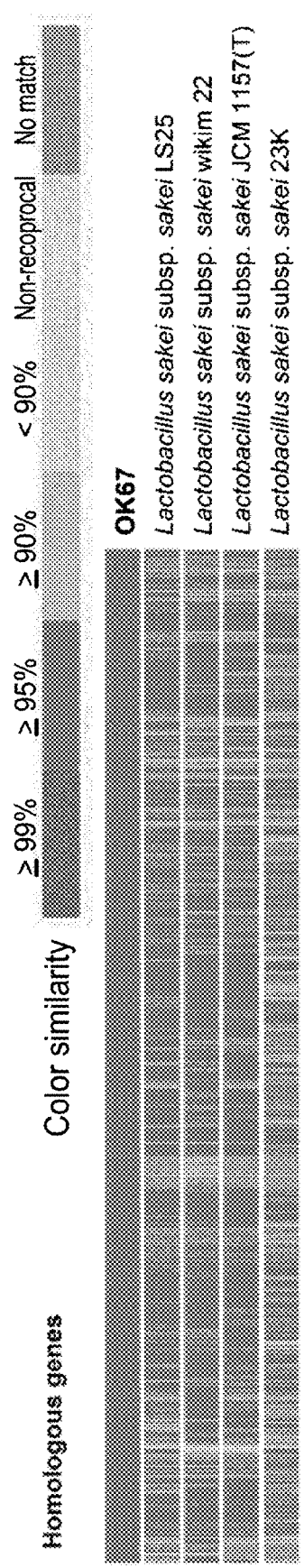
FIG. 34 illustrates the distribution of homologous genes between strains similar to *Lactobacillus sakei* OK67.

*Lactobacillus sakei* OK67 was inoculated into 500 ml of MRS broth medium and cultured for 24 hours. The cells were harvested from the culture solution, DNA was extracted, and the entire genome sequence was analyzed using Illumina HiSeq 2500 (Illumina CS Pro). The entire genome sequence of *Lactobacillus sakei* OK67 was identical to the nucleotide sequence as set forth in SEQ ID NO: 2 and its length was 1,781,778 bp. FIG. 33 illustrates a comparison of the average nucleotide identity (ANI) values between strains similar to *Lactobacillus sakei* OK67. In addition, FIG. 34 illustrates the distribution of homologous genes between strains similar to *Lactobacillus sakei* OK67. In FIGS. 33 and 34, the term "OK67" refers to *Lactobacillus sakei* OK67. As illustrated in FIGS. 33 and 34, *Lactobacillus sakei* ok67 taxonomically falls within the same species as *Lactobacillus sakei* subsp. *sakei* LS25, *Lactobacillus sakei* subsp. *sakei* wikim 22, *Lactobacillus sakei* subsp. *sakei* JCM 1157(T), *Lactobacillus sakei* subsp. *sakei* 23K, and the like, but is genetically different significantly.

10. Production of Pharmaceutical Compositions Including Lactic Acid Bacteria and the Like The *Lactobacillus sakei* OK67 culture in the preparation of the following pharmaceutical composition may be replaced by *Lactobacillus sakei* OK67 strain itself, its lysate or its extract.

<10-1> Preparation of Powders

*Lactobacillus sakei* OK67 culture 20 mg

Lactose 100 mg

Talc 10 mg

The above components were mixed and packed in airtight bags to prepare powders.

<10-2> Preparation of Tablets

*Lactobacillus sakei* OK67 culture 10 mg

Corn starch 100 mg

Lactose 100 mg

Magnesium stearate 2 mg

After mixing the above components, the tablets were prepared by tableting the same according to a conventional method for preparing tablets.

<10-3> Preparation of Capsules

*Lactobacillus sakei* OK67 culture 10 mg

Crystalline cellulose 3 mg

Lactose 15 mg

Magnesium stearate 0.2 mg

After mixing the above components, the capsules were prepared by filling the same in gelatin capsules according to the conventional method for preparing capsules.

<10-4> Preparation of Pills

*Lactobacillus sakei* OK67 culture 10 mg

Lactose 150 mg

Glycerin 100 mg

Xylitol 50 mg

After mixing the above components, they were prepared to be 4 g per one pill according to the conventional method.

<10-5> Production of granules

*Lactobacillus sakei* OK67 culture 15 mg

Soybean extract 50 mg

Glucose 200 mg

Starch 600 mg

After mixing the above components, 100 mg of 30% ethanol was added and the mixture was dried at 60° C. to form granules, which were then filled in a capsule.

<10-6> Preparation of injections

*Lactobacillus sakei* OK67 culture 10 mg

Sodium metabisulfite 3.0 mg

Methyl paraben 0.8 mg

Propyl paraben 0.1 mg

Suitable amount of sterile distilled water for injection

After mixing the above components, 2 ml of the mixture was filled in an ampoule and sterilized to prepare an injection.

11. Preparation of Food Composition Including Lactic Acid Bacteria and the Like

In the following preparation of a food composition, a *Lactobacillus sakei* OK67 culture may be replaced with *Lactobacillus sakei* OK67 strain itself, a lysate thereof or an extract thereof <11-1> Preparation of Flour Food To 100 parts by weight of wheat flour, 0.5 part by weight of *Lactobacillus sakei* OK67 culture was added to wheat flour, and the mixture was used to prepare bread, cake, cookies, crackers and noodles.

<11-2> Preparation of Dairy Products

With respect to 100 parts by weight of milk, 0.5 part by weight of *Lactobacillus sakei* OK67 culture was added to milk, and the milk was used to make various dairy products such as butter and ice cream.

<11-3> Preparation of Sunsik Product (Health Food)

Brown rice, barley, glutinous rice, and Job's tears were pregelatinized and dried by a known method and then roasted, and then were prepared into powder having a particle size of 60 mesh by a pulverizer.

Black beans, black sesame seeds, and *perilla* seeds were steamed and dried by a known method and then roasted, and then were prepared into powder having a particle size of 60 mesh by a pulverizer.

The above-prepared cereals, seeds and *Lactobacillus sakei* OK67 culture were prepared by blending the same at a following ratio.

Cereals (30 parts by weight of brown rice, 17 parts by weight of Job's tears, 20 parts by weight of barley), Seeds (7 parts by weight of *perilla* seeds, 8 parts by weight of black beans, 7 parts by weight of black sesame seeds),

*Lactobacillus sakei* OK67 culture (1 part by weight),

*Ganoderma Lucidum* (0.5 part by weight),

Foxglove (0.5 parts by weight)

<11-4> Preparation of healthy drinks 1 g of *Lactobacillus sakei* OK67 culture was homogenously blended with minor ingredients such as liquid fructose (0.5 g), oligosaccharide (4 g), sugar (2 g), table salt (0.5 g) and water (77 g), and was sterilized instantaneously and packaged in a small packing container such as a glass bottle or a PET bottle.

<11-5> Preparation of Vegetable Juice

Vegetable juice was prepared by adding 2 g of the fermented *Coconopsis lanceolata* extract of Preparation Example 2 to 1,000 ml of tomato or carrot juice.

<11-6> Preparation of Fruit Juice

Fruit juice was prepared by adding 1 g of *Lactobacillus sakei* OK67 culture to 1,000 ml of apple or grape juice.

12. Deposit Information of Lactic Acid Bacteria

On Feb. 23, 2015, the inventors of the present invention deposited a patent on *Lactobacillus sakei* OK67 on the basis of the Budapest Treaty to the Korean Culture Center of Microorganisms (address: Yurim Building, 45, Hongjenae 2ga-gil, Seodaemun-gu, Seoul, Republic of Korea), which is an authorized depository institution, and were given an accession number of KCCM 11670P.

From the foregoing, the present invention has been described by way of the above examples but is not limited thereto. It is apparent that various modifications may be made without departing from the scope and spirit of the present invention. Therefore, the protection scope of the present invention should be construed as including all embodiments falling within the scope of the appended claims.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11104878B2). An electronic copy of the "Sequence Listing" will also be available from the USPTO upon request and payment of the fee set forth in 37 CFR 1.19(b)(3).

The invention claimed is:

1. A method for alleviating or treating obesity, which comprises administering to a subject in need thereof an effective amount of a composition comprising an active ingredient consisting of *Lactobacillus sakei* OK67 (accession number: KCCM 11670P) strain or a culture thereof, wherein the content of *Lactobacillus sakei* OK67 (accession number: KCCM 11670P) strain is 0.1 to 99% by weight based on the total weight of the composition.

2. The method according to claim 1, wherein the composition is a pharmaceutical composition or a food composition.

3. The method according to claim 1, wherein the method further alleviates or treats at least one selected from the group consisting of diabetes, hypertriglyceridemia, hypercholesterolemia, hyperlipidemia, dyslipidemia, arteriosclerosis, metabolic syndrome, an inflammatory disease and liver damage.

* * * * *